(12) United States Patent
Haupt et al.

(10) Patent No.: US 9,956,542 B2
(45) Date of Patent: May 1, 2018

(54) METHOD FOR PREPARING MOLECULARLY IMPRINTED POLYMERS (MIP) THROUGH RADICAL POLYMERISATION

(75) Inventors: Karsten Haupt, Pronleroy (FR); Arnaud Cutivet, Villeurbanne (FR); Jeanne Bernadette Tse Sum Bui, Pronleroy (FR); Pinar Cakir, Compiegne (FR)

(73) Assignee: Universite de Technologie de Compiegne—UTC, Compiegne (FR)

(*) Notice: Subject to any disclaimer, the term of this patent is extended or adjusted under 35 U.S.C. 154(b) by 1113 days.

(21) Appl. No.: 13/062,608

(22) PCT Filed: Sep. 1, 2009

(86) PCT No.: PCT/FR2009/001051
§ 371 (c)(1),
(2), (4) Date: Dec. 22, 2011

(87) PCT Pub. No.: WO2010/026308
PCT Pub. Date: Mar. 11, 2010

(65) Prior Publication Data
US 2012/0100358 A1 Apr. 26, 2012

(30) Foreign Application Priority Data
Sep. 5, 2008 (FR) ..................... 08 04874

(51) Int. Cl.
*B01J 20/26* (2006.01)
*C07C 333/20* (2006.01)
(Continued)

(52) U.S. Cl.
CPC ........... *B01J 20/268* (2013.01); *C07C 333/20* (2013.01); *C07D 249/04* (2013.01); *C08F 2/38* (2013.01);
(Continued)

(58) Field of Classification Search
CPC ...... C08F 2/38; C08F 2/48; C08F 2/50; C08F 2810/20; C08F 222/1006; B01J 20/26; B01J 20/268
See application file for complete search history.

(56) References Cited

U.S. PATENT DOCUMENTS 4,505,794 A * 3/1985 Kvita et al. ............... 522/14
4,777,191 A * 10/1988 Komai .............. C07C 409/38
522/104

(Continued)

FOREIGN PATENT DOCUMENTS

EP 1 767 551 A1 3/2007

OTHER PUBLICATIONS

Schmidt, Ronald H. and Karsten Haupt, "Molecularly Imprinted Polymer Films with Binding Properties Enhanced by the Reaction INduced Phase Separation of a Sacrificial Polymeric Porogen", Feb. 2, 2005, Chemical Materials, 17, 1007-1016.*

(Continued)

*Primary Examiner* — Bijan Ahvazi
*Assistant Examiner* — David L Miller
(74) *Attorney, Agent, or Firm* — Brian L. Stender; Patterson Thuente Pederson, P.A.

(57) ABSTRACT

The invention relates to a method for preparing molecular imprint polymers (MIP) by radical polymerization that uses at least one primer including at least two chemical functions capable of forming reactive radicals, thereby providing a locally high radical concentration for priming the polymerization on or about the imprint entity or molecule. The invention also relates to molecular imprint polymers (MIP) that can be obtained by the method of the invention, and to the use thereof in the production of biomimetic biosensors, (Continued)

biomimetic biochips, chemical sensors, specific adsorption separation devices, as a coating, particularly for releasing active ingredients.

15 Claims, 17 Drawing Sheets

(51) Int. Cl.
  C07D 249/04 (2006.01)
  C08F 2/38 (2006.01)
  C08F 2/48 (2006.01)
  C08F 8/14 (2006.01)
  C08F 8/30 (2006.01)
  C08F 8/34 (2006.01)
  C08F 2/50 (2006.01)
  C08F 222/10 (2006.01)

(52) U.S. Cl.
  CPC ............... C08F 2/48 (2013.01); C08F 8/14 (2013.01); C08F 8/30 (2013.01); C08F 8/34 (2013.01); B01J 20/26 (2013.01); C08F 2/50 (2013.01); C08F 222/1006 (2013.01); C08F 2810/20 (2013.01); Y10T 428/249953 (2015.04); Y10T 428/2982 (2015.01)

(56) References Cited

U.S. PATENT DOCUMENTS

| | | | |
|---|---|---|---|
| 5,760,149 A * | 6/1998 | Sanchez | C07C 409/38 525/313 |
| 5,973,181 A * | 10/1999 | Ishigaki | C08F 4/36 526/230.5 |
| 6,379,599 B1 | 4/2002 | Vaidya et al. | |
| 6,525,154 B1 * | 2/2003 | Shea et al. | 526/307.2 |
| 2003/0003587 A1 * | 1/2003 | Murray | G01N 21/7703 436/82 |
| 2003/0129092 A1 * | 7/2003 | Murray | 422/82.07 |
| 2005/0037277 A1 * | 2/2005 | Herlihy | C07C 69/712 430/270.1 |
| 2005/0245624 A1 * | 11/2005 | Busson | B01J 20/26 521/50 |

OTHER PUBLICATIONS

Bossi, Alessandra et al. "'Gate effect' in templated polyacrylamide membranes influences the electrotransport of proteins and finds applications in proteome analysis", Apr. 2007, Analytical and Bioanylytical Chemistry, vol. 389 Iss 2, 3447-454.*

Qin, "A Novel Photo-Initiating System for Atom Transfer Radical Polymerization of Styrene", Chinese Journal of Polymer Science, vol. 19, No. 5, (2001), pp. 441-445.

Antonietti et al., "Properties of Fractal Divinylbenzene Microgels", Macromolecules, 1991, 24, pp. 3434-3442.

Biffis et al., "The Synthesis, Characterization and Molecular Recognition Properties of Imprinted Microgels," Macromol. Chem. Phys., 2001, 202, pp. 163-171.

Gale et al., "Mechanism of Diethyldithiocarbamate, Dihydroxyethyldithiocarbamate, and Dicarboxymethyldithiocarbamate Action on Distribution and Excretion of Carmium," Annals of Clinical and Labroatory Science, vol. 13, No. 6, 1983, pp. 474-481.

Ju et al., "Revisiting Nucleophilic Substitution Reactions: Microwave-Assisted Synthesis of Azides, Thiocyanates, and Sulfones in an Aqueous Medium", J. Org. Chem., 2006, 71, pp. 6697-6700.

Kolb et al., "The growing impact of click chemistry on drug discovery", DDT, Dec. 2003, vol. 8, No. 24, pp. 1128-1137.

Kolb et al., "Click Chemistry: Diverse Chemical Function from a Few Good Reactions", Angew. Chem. Int. Ed., 2001, 40, pp. 2004-2021.

Mehrotra, "Present Status and Future Potential of the Sol-Gel Process", Department of Chemistry, University of Rajasthan, Jaipur 302004, India, 1992, 36 pages.

Mosbach et al., "The Emerging Technique of Molecular Imprinting and Its Future Impact on Biotechnology", Biotechnology, Feb. 1996, vol. 14, pp. 163-170.

Otsu, "Iniferter Concept and Living Radical Polymerization", Journal of Polymer Science: Part A: Polymer Chemistry, 2000, vol. 38, pp. 2121-2136.

Rückert et al., "Molecularly imprinted composite materials via iniferter-modified supports", J. Mater. Chem., 2002, 12, pp. 2275-2280.

Schmidt et al., "Molecularly Imprinted Polymer Films with Binding Properties Enhanced by the Reaction-Induced Phase Separation of a Sacrificial Polymeric Porogen", Chem. Mater., 2005, 17, pp. 1007-1016.

Wulff et al., "Soluble Single-Molecule Nanogels of Controlled Structure as a Matrix for Efficient Artificial Enzymes", Angew Chem. Int. Ed., 2006, 45, pp. 2955-2958.

* cited by examiner

METHOD FOR PREPARING MOLECULARLY IMPRINTED POLYMERS (MIP) THROUGH RADICAL POLYMERISATION

PRIORITY CLAIM

The present application is a National Phase entry of PCT Application No. PCT/FR2009/001051, filed Sep. 1, 2009, which claims priority from French Application No. 08/04874, filed Sep. 5, 2008, the disclosures of which are hereby incorporated by reference herein in their entirety.

TECHNICAL FIELD OF THE INVENTION

The present invention relates to a method for preparing a molecularly imprinted polymer(s) (MIP) through radical polymerization that uses at least one initiator comprising at least two chemical functionalities capable of forming reactive radicals, thereby, providing a locally high concentration of radicals for initiating the polymerization over or around the imprinting molecule or entity.

The present invention also relates to a molecularly imprinted polymer(s) (MIP) liable to be obtained by the method of the invention as well as their use for making biomimetic biosensors, biomimetic biochips, chemical sensors, specific adsorption separation devices, as a coating, in particular, for salting out active products.

BACKGROUND OF THE INVENTION

Chemical sensors or biosensors are devices that are able to retain at least temporarily a chemical or biological substance to detect and/or to quantify as for example the measure or detection of a gas (measurement of pollution, chemical reagents, etc.), the detection of an active principle (drug, herbicide, etc.), the detection of human or animal substances (cells, proteins, etc.), viruses, etc.

Biosensors and the currently available stationary phases separated based on affinity often use biomacromolecules or biological macromolecules as specific recognition elements, particularly antibodies, enzymes or nucleic acids. Said biomacromolecules have a weak chemical and physical stability, in particular to organic solvents, acid and bases and high temperatures. The biomacromolecules are expensive, difficult to obtain and difficult to integrate into industrial manufacturing processes. In this context, the use of polymers and/or copolymers having one or several types of molecular imprint(s) (MIP) establishes itself as an alternative to these biomacromolecules. They are biomimetic material which reproduces the molecular recognition capability observed in certain biological macromolecules [1].

Polymers having one or several types of molecular imprint(s) (MIP) already exist. However, their practical usage is inhibited by an over complex implementation in the optimal form for the related application.

The synthesis of polymers through radical polymerization using relatively weak concentrations of initiator and monomers, as in the case of the initiator immobilized on a solid support [2] or in a diluted solution for the synthesis of microgels and nanogels [3] has already been described. The obtained polymer usually has a "fractal" shape that is not sufficiently dense for its adaptation to the synthesis of the MIP [4].

For the synthesis of MIP polymers in the form of microgels, it has been proposed to overcome this drawback, first by using a high concentration of reagents to dilute the solution just before the macro-gel process in order to obtain dense microgels [5]. Yet, this approach is tricky and difficult to implement especially in an industrial context, due to the fact that a scale-up seems difficult to achieve in a reproducible manner.

Hence, there exists a real need for a method for preparing molecularly imprinted polymer(s) (MIP) to overcome these faults, drawbacks and obstacles of the prior art.

Particularly, there exists a real need for a method that is reproducible, industrially achievable, which makes it possible to prepare molecularly imprinted polymer(s) (MIP) in a manner that is dense and localized, on a micro or nanometric scale, which further may allow for a monitoring of the size, morphology and shape of the obtained polymers (MIP).

BRIEF SUMMARY OF THE INVENTION

The present invention is directed at a method for preparing one or more molecularly imprinted polymer, the molecularly imprinted polymer is prepared by contacting at least one imprinting molecule or entity with one or more identical or different monomers and at least one initiator. The monomers are capable of forming the molecularly imprinted polymer, and the initiator has at least two chemical functionalities that are capable of forming radicals for initiating a polymerization of the one or more monomers over or around the at least one imprinting molecule or entity. Once the imprinting molecule or entity, monomers, and initiator are contacted, radical polymerization of the one or more monomers is performed over or around the at least one imprinting molecule or entity to form the molecularly imprinted polymer over or around the at least one imprinting molecule or entity. In some aspects, the radical polymerization is performed under exposure of light irradiation of visible or UV wavelength or a supply of thermal energy. After the polymerization to form the molecularly imprinted polymer, any non-polymerized monomer and/or all or a portion of the imprinting molecule or entity can be removed by a solvent or mixture of solvents.

In some aspects, the imprinting molecule or entity is chosen from amino acids, monosaccharide, lipids, nucleosides, nucleotides, oligomers and polymers obtained from entities or molecules, in particular, peptides, proteins, nucleic acids, oligosaccharides, polysaccharides; biologically active entities or molecules, in particular drugs, particularly antibiotics, steroids, vitamins, toxins, enzymes, doping agents, pesticides, insecticides, fungicides, herbicides; explosive substances; toxic substances; endoctrine perturbators; bacterial mycotoxins and toxins; nanoparticles; prokaryotic and eukaryotic bacteria cells; animal cells, in particular yeast cells, fungus cells, and human and animal cells; plant cells; viruses; and cellular tissues. In some aspects, the imprinting molecule or entity is chosen from trypsin, kallikrein, S-propranolol, theophyllin, 2,4-dichlorophenoxyacetic acid, beta-estradiol, testosterone, atrazine, morphine, cocaine, and tetrahydrocannabinol.

In some aspects, a substrate may be added during the preparation method such that the imprinting molecule or entity, the initiator, and/or the molecularly imprinted polymer while forming, may attach onto the substrate. In some aspects, the substrate comprises glass, quartz, mica, silicon, germanium, silicon carbide, tin-indium oxide, titanium dioxide, aluminum oxide, an organic polymer that may be crosslinked, particularly, polystyrene, poly(styrene-co-methacrylate), poly(methyl methacrylate), poly(acrylonitrile), polyamide, polyester, polyurethane, poly(dimethyl siloxane), polybutadien, or a metal, such as gold, silver, platinum, and a composite of two or more of these materials.

In some aspects, the initiator comprises up to 64 chemical functionalities, preferably from 2 to 16 chemical functionalities, and more preferentially from 4 to 8 chemical functionalities, capable of forming radicals for initiating the polymerization of the monomers over or around the imprinting molecule or entity.

In some aspects, the initiator may be in a mixture containing a sensitizer compound.

In some aspects, the contacting step may be conducted in the presence of a pore-forming agent that forms pores in the molecularly imprinted polymer.

The present invention is also directed at molecularly imprinted polymers obtainable by the radical polymerization method.

In some aspects, the molecularly imprinted polymer is in the form of a film having a thickness between 1 nm and 100 µm. In some aspects, the molecularly imprinted polymer is in the form of spherical particles having a diameter between 1 nm and 100 µm. In some aspects, the molecularly imprinted polymer has a porous structure, the pores of the porous structure having a pore diameter between 0.1 nm and 10 µm.

The present invention is also directed at molecular imprinted polymers obtainable by the radical polymerization method, the molecular imprinted polymers used as a coating on biomimetic biosensors, biomimetic biochips, chemical sensors, and specific adsorption separation devices, in particular, for salting out active products.

Figure 14:
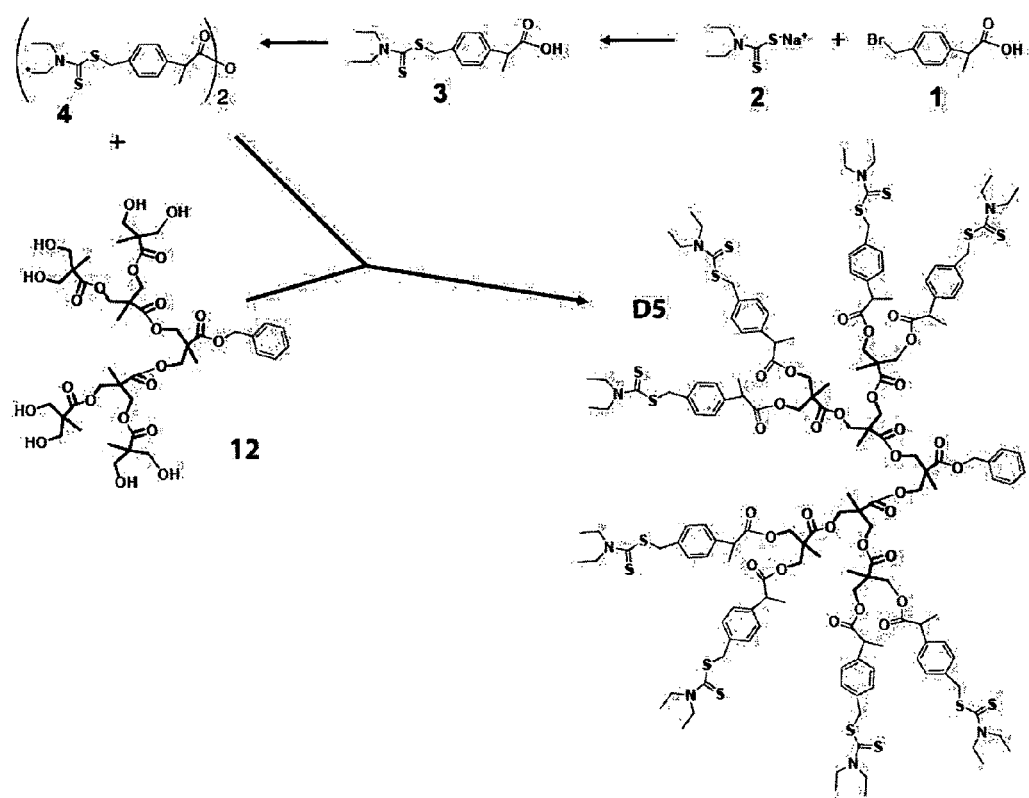

FIG. 14 illustrates the chemical structure and the synthesis pathway of the molecule D5, the specific initiator molecule described in example 1. D5 is synthesized on the basis of a dendritic structure wherein the functionalities (F1) at the periphery allowing to generate reactive radicals and therefore to initiate a radical polymerization, are 8 benzyl diethyldithiocarbamate functionalities (iniferter-type initiator for living radical polymerization).

Figure 15A:
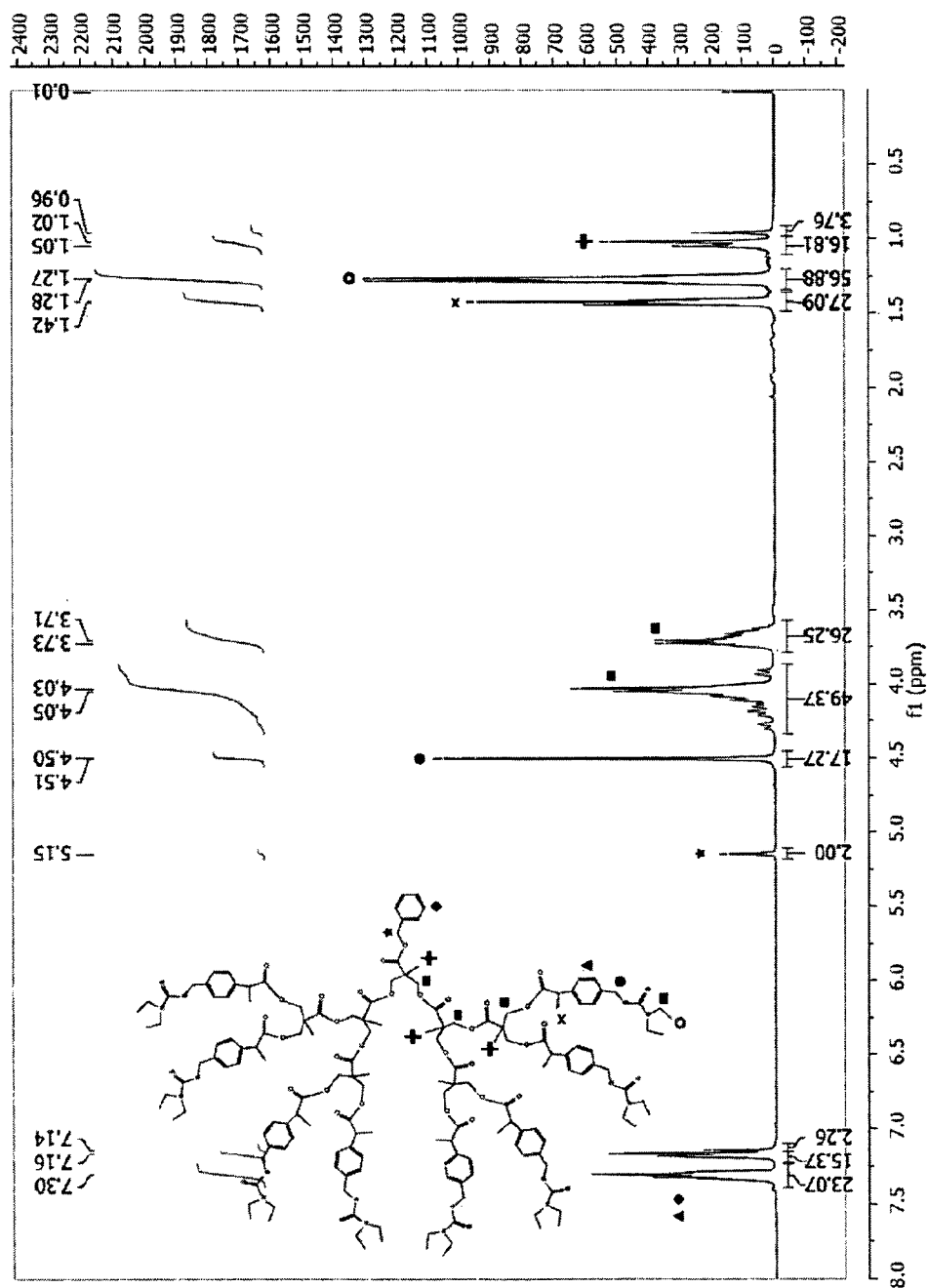
Figure 15B:
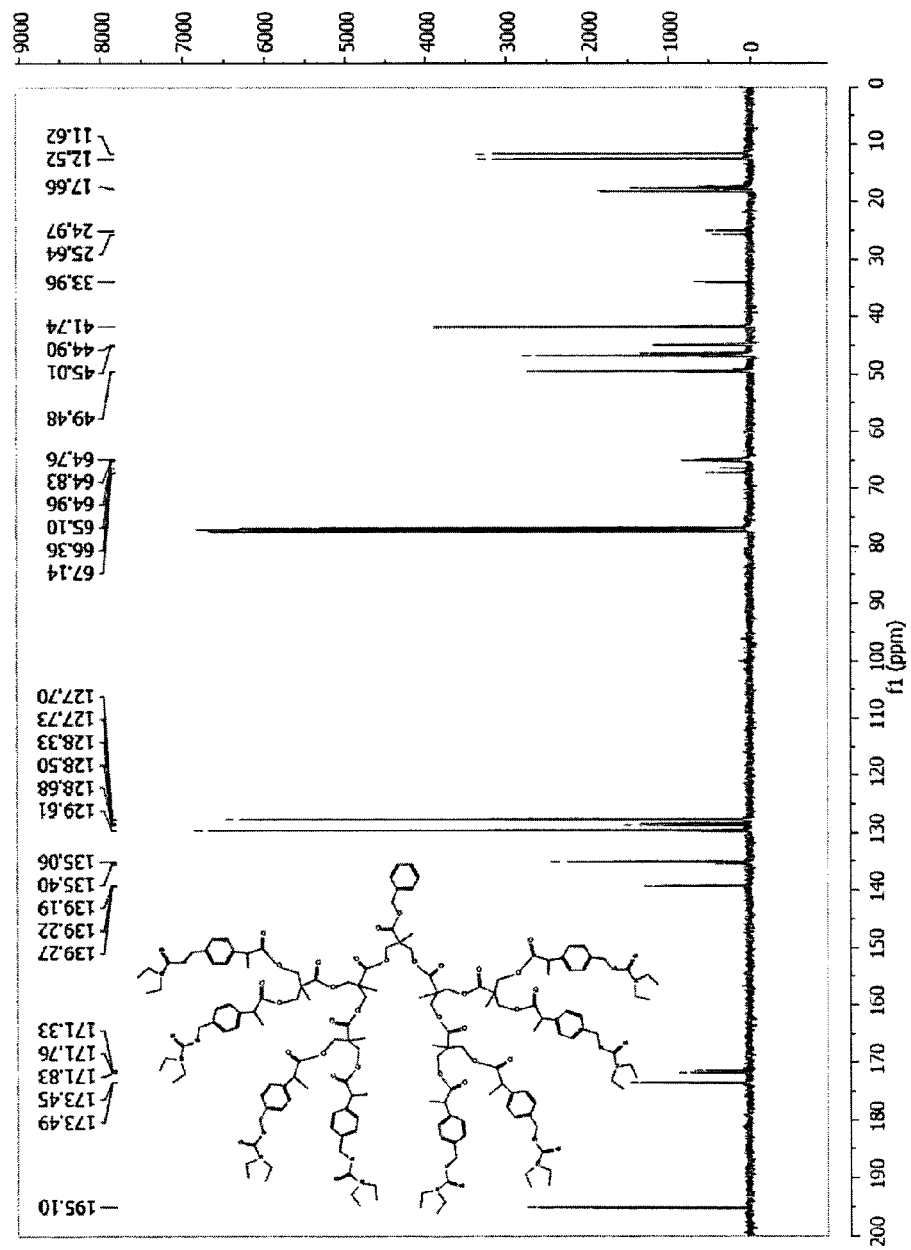

FIGS. 15A and 15B illustrate proton (FIG. 15A) and carbon (FIG. 15B) nuclear magnetic resonance spectra of D5.

DESCRIPTION OF THE INVENTION

The object of the present invention is specifically to meet this need by providing a process for preparing a molecularly imprinted polymer(s) (MIP) through radical polymerization wherein:

a) are contacted with each other:
  at least one imprinting molecule or entity;
  identical or different monomers, capable of forming the molecularly imprinted polymer(s) (MIP);
  at least one initiator including at least two chemical functionalities (F1) capable of forming radicals for initiating the polymerization of said monomers over or around said imprinting molecule or entity;

b) a polymerization under exposure to light irradiation of visible or UV wavelength or with supply of thermal energy is performed thereby forming over or around said imprinting molecule or entity a molecularly imprinted polymer(s) (MIP);

c) non polymerized monomer or monomers and/or all or part of the imprinting molecule or entity of the polymer formed in b) are removed with a solvent or a convenient mixture of solvent or solvents.

The polymerization method according to the present invention implements a new type of initiator for preparing molecularly imprinted polymer(s) (MIP), allowing a localized generation of a high number of radicals and a good mastery of the size, shape and morphology of macromolecular chains during polymerization.

This helps to improve the polymers (MIP) properties and thus, at the same time optimize the recognition selectivity and the response sensitivity of a device based on such a polymer (MIP).

Molecularly imprinted polymer(s) (MIP) is/are obtained based on the principle of molecular imprinting. Molecular imprinting is a well-known technique by the skilled person. It globally consists in its fundamental principle to create complementary images to a molecule in a material, in general a synthetic polymer. The molecule(s) or entity(s) against which imprints must be generated (molecule or entity imprinted according to the present invention) are put in contact with a monomer mixture bearing functional groups capable of complexing said molecule(s) or entities by non-covalent bonds, by coordinate bonds or by reversible covalent bonds.

As it will be explained in further detail hereafter, it is essential that the nature of the bond of each entity or molecule imprinted with the MIP be reversible such as to be able, in determined conditions, to detach or unbind said entity/ies or molecules of the polymer or imprinted material(s) one wishes to synthesize and which will then serve to detect, sense and/or salt the pertinent substances based on the application or the required usage.

In the description, the terms polymer and molecularly imprinted material(s) may be used interchangeably. By polymer or material, according to the present invention, it is to be understood that all types of polymers, homopolymers (synthesized based on one single type of monomer and whereof all the repeat units are of the same chemical nature), copolymers (a polymer containing several types of repeat units), organic or inorganic, are usually used for this type of technique.

According to the present invention, a radical is a chemical species having one or several unpaired electrons. The presence of a single electron gives these species a high reactivity, meaning that they may react with other compounds.

Furthermore, in the rest of the written description, the terms "to attach" and "to bind" are used interchangeably to mean the bond which forms between atoms and molecules. Depending on the case, it may be: covalent, coordinate, hydrogen, ionic, Van der Waals bond or a hydrophobic interaction. Depending on the cases, the bond may be reversible or not.

Within the scope of the present invention, by dendron is meant an arborescent molecule constructed by iterative processes (that can reproduce several times) based on a molecule comprising, on the one hand branching structures with reactive extremities and on the other hand, a site able to attach on a molecular or solid support. The size of the dendron is a function of the number of iterations also called generation. The greater the number of iterations or generations, the larger the dendron will be. A generation x corresponds to x iterations, x being an integer corresponding to the number of iterations. The more important the dendron generation, the higher the number of reactive extremities will be.

By dendritic is meant a dendron-type structure. The term iniferter, (In English "initiator—Transfer agent—Terminator" and in French "Agent initiateur, de Transfert et de Terminaison") designates a type of initiator for living radical polymerization such as described in the reference [6].

As indicated, monomer polymerization may be done over the imprinting molecule or entity or around it.

The polymerization is done over the imprinting molecule or entity when the formed polymer(s) are directly binded to said entity or molecule and only partially coat it. This may occur particularly when the imprinting molecule or entity and the polymer(s) formed are of neighboring dimensions. This may be seen for example if a polymer (MIP) in the form of nanometric-size particles is synthesized for a protein as imprinting molecule which itself has a diameter of a few nanometers. This may also occur when the imprinting molecule or entity is attached on a support during the polymer (MIP) synthesis and hence has restricted accessibility.

The polymerization is done around the imprinting molecule or entity when the formed polymer(s) is/are directly binded to said entity or molecule and coat it completely at the end of the polymerization. An example is a polymer (MIP) in the form of nanoparticles for a small imprinting molecule such as an amino acid; in this case the polymer (MIP) has a larger size by one or several orders of magnitude than the imprinting molecule.

In step a), the imprinting molecule or entity is intended to generate in the polymer molecular imprints, the result being a molecularly imprinted polymer(s) (MIP). According to the present invention, this is called the entity or target molecule, the entity or molecule intended to be binded in a reversible manner to the molecularly imprinted polymer (MIP) during its use.

The imprinting molecule or entity may be identical to the entity or target molecule. It may also be a derivative in structure and form close to the entity or target molecule. The imprinting molecule or entity may further correspond to only a part of the entity or target molecule.

Any type of imprinting module or entity may be used in the method of the invention.

More particularly, the imprinting module or entity may be chosen in the group comprising:
- amino acids, monosaccharide, lipids, nucleosides, nucleotides, oligomers and polymers obtained from these entities or molecules, in particular, peptides, proteins, nucleic acids, oligosaccharides and polysaccharides;
- biologically active entities or molecules, in particular drugs, particularly, antibiotics, steroids, vitamins, toxins, enzymes, doping agents, pesticides, insecticides, fungicides and herbicides,
- explosive substances,
- toxic substances,
- endocrine perturbators,
- bacterial mycotoxins and toxins,
- nanoparticles,
- prokaryotic and eukaryotic bacteria cells,
- animal cells, in particular, yeast cells, fungus cells, and human and animal cells,
- plant cells,
- viruses, and
- cellular tissues.

More specifically, the imprinting molecule or entity may be selected from the group comprising typsin, kallikrein, S-propranolol, theophylline, 2,4-dichlorophenoxyacetic acid, beta-estradiol, testosterone, atrazine, morphine, cocaine, tetrahydrocannabinol.

Within the scope of the present invention, it is possible to make materials having only one and unique type of imprint (intended to only attach one single imprinting molecule or entity, just as one may provide several different types of imprints (for example for a series of molecules who are similar in nature and size or which have a same type of chemical functionality or biological receptor), and thus whatever the density of the imprint or the different types of imprints present at the surface and or in the material (cage, tridimensional network), that is to say the number of imprints per $m^2$ or $m^3$.

Naturally, one may make the density vary according to the type of imprint if the available material has several types of different imprints.

According to a specific embodiment, in step a), a part from the imprinting molecule or entity, one may also add a preferably solid substrate. In this embodiment, the imprinting molecule or entity, the initiator and/or the molecularly imprinted polymer (MIP) while forming, may attach themselves onto this substrate.

According to the present invention, by substrate is meant any solid material, soluble or not, or any liquid material, able to serve as support and enabling the fixation of the initiator and/or the polymer (MIP).

The substrate may advantageously be a homogenous and isotropic support substrate or a non-homogenous material or of composite type.

The substrate may be chosen from the group comprising glass, quartz, mica, silicon, germanium, silicon carbide, tin-indium oxide, titanium dioxide, aluminum oxide, an organic polymer which may be cross-linked, particularly, polystyrene, poly(styrene-co-methacrylate), poly(methyl methacrylate), poly(acrylonitrile), polyamide, polyester, polyurethane, poly(dimethyl siloxane), polybutadien, or a metal, particularly, gold, silver, platinum, or a composite of two or more of these materials.

To implement the method according to the present invention, every monomer comprising at least a polymerizable function through radical polymerization, may be suitable. The skilled person will easily know to select the monomers, known per se, which will be appropriate for the implementation of the method according to the present invention.

More specifically, in the method according to the present invention, the monomers bear functional groups capable of forming reversible bonds with the entity/ies or imprinting molecules, by one or several non covalent bonds of hydrogen, ionic, van der Waals type, or by hydrophobic interaction, or by one or several coordinate or covalent bonds.

The monomers according to the present invention may be "binding monomers" possibly in a mixture with "cross-linked monomers".

According to the present invention, by "binding monomer" is meant a monomer capable of forming in a reversible manner, at least a weak coordinate and/or covalent bond with the imprinting molecule or entity, thus ensuring a reversible bond between said imprinting molecule or entity and the molecularly imprinted polymer obtained from the method.

The weak coordinate and/or covalent bond between the binding monomers and the imprinting molecule or entity may be formed through a functionality selected from the group comprising functionalities of hydroxyl, acid, ester, amide, amine, thiol, ether, amidine, guanidine, aldehyde and ketone, urea, thiourea, pyridine, imidazole, metal chelate, said functionality being present on the fixing monomer and/or the cross-link monomer.

By "cross-link monomer" is meant, a bi- or multifunctional monomer comprising at least two polymerizable functionalities through radical polymerization, capable of permanently forming, covalent bonds, with other binding monomers and/or cross-linked monomers thus resulting in a polymer with a tridimensional network polymer constituting the molecularly imprinted polymer (MIP).

In step a), monomers, be they binding or cross-linking, may comprise at least one vinyl function or another ethylenic function adapted to a radical polymerization.

Preferably, these monomers comprising at least a vinyl function are selected from the group comprising: methacrylic acid, trifluoromethyl acrylic acid, acrylic acid, itaconic acid, styrene sulfonic acid, acrylamido methylpropane sulfonic Acid, 4-vinyl phenyl boronic acid, 4-vinylbenzoic acid, carboxyethyl acrylate, hydroxyethyl methacrylate phosphate, 2-vinylpyridine, 4-vinylpyridine, 1-vinylimidazole, 4(5)-vinylimidazole, 2-amino ethyl methacrylate, 2-(dimethylamino ethyl)methacrylate, aminoethyl acrylate, 4-vinylbenzyl trimethylammonium chloride, hydroxyethyl methacrylate, glycidyl methacrylate, acrylamide, methacrylamide, isopropylacrylamide, 4-vinylbenzamidine, 4-methacrylamide benzamidine, styrene, phenyl methacrylate, cyclohexyl methacrylate, methyl methacrylate, butyl methacrylate, hexyl methacrylate, octyl methacrylate, ethylene glycol dimethylacrylate, hexanediol dimethacrylate, trimethylolpropane trimethacrylate, polyethylene glycol dimethacrylate, triethylene glycol dimethacrylate, pentaerythritol triacrylate, divinylbenzene, ethylene bisacrylamide, methylenebisacrylamide, bis acryloyl piperazine, N N'-bis acryloyl cystamine, N,N'-1,2 dihydroxyethylene-bis acrylamide, N,O-bismethacryloyl ethanolamine, or a mixture of these.

The monomers of the invention may also be selected from the group comprising hybrid monomers comprising a vinyl polymerizable function through radical polymerization and a silane-type function polymerizable by a sol-gel process such as for example 3-methacryloxypropyltrimethoxysilane.

By sol-gel process, is meant a process leading to a low temperature elaboration of transparent and dense amorphous solids, wherein organic molecular species may be introduced thus, making it possible to develop new organic-inorganic hybrid material. This type of process is particularly described in [7], the process of which is incorporated by reference.

As previously indicated, in step a), at least an initiator comprising at least two chemical functionalities capable of forming radicals for initiating polymerization is used.

Thus, the initiator used is a radical polymerization initiator advantageously comprising at least two or even several chemical functionalities that are able to form radicals simultaneously. At the same time, this initiator may advantageously comprise one or several chemical functionalities (F2) that allow it to covalently or non covalently attach on the imprinting molecules or entities with molecular imprinting, or on a substrate. Accordingly, the present invention makes it possible to prepare a molecularly imprinted polymer(s) in a dense and localized manner over or around imprinting molecule(s) or entity/entities.

As previously indicated, in step a), at least an initiator comprising at least two chemical functionalities (F1) capable of forming radicals for initiating the polymerization of monomers over or around the imprinting molecule or entity is used.

The initiator may comprise up to 64 functionalities (F1), preferably from 2 to 16, and more preferentially from 4 to 8 chemical functionalities (F1) capable of forming radicals for initiating the polymerization of monomers over or around the imprinting molecule or entity.

The chemical functionalities (F1) of the initiator capable of forming radicals for initiating polymerization may be added for example by a component selected from the group comprising:

benzoin ethers particularly benzoin methyl ether, benzoin ethyl ether, benzoin butyl ether, benzoin isopropyl ether, acetophenones in particular 2-2-dimethoxy-2-phenylacetophenone, 2-hydroxy-2methyl-1-phenyl-propan-1one or 2-methyl-1-[4-(methylthio)-phenyl]-2-morpholinopropan-1-one, substituted benzophenones;

substituted peroxides particularly bis(tert-butylcyclohexyl)peroxydicarbonate, derivatives of phosphine-oxides in particular bis(2,4,6-trimethylbenzoyl)-phenyl-phosphine-oxide, amino-ketones, oxysulfonyl-ketones, sulfonyl-ketones or one these derivatives, and azo-type compounds particularly azo-bis-isobutyronitrile, azo-bis-dimethylvaleronitrile, 4,4'-Azobis(4-cyanovaleric acid), 2,2'-azobis(2-aminopropane);

hydroxyalkylamines particularly methyldiethanolamine, benzylamines, aniline derivatives, ethyl para-dimethylaminobenzoate, N-phenylglycine (NPG);

ascorbic acid;

a derivative of dithiocarbamate particularly benzyl-N,N-dimethyldithiocarbamate, benzyl-N,Ndiethyldithiocarbamate, benzyl-N,N-di(carboxymethyl)dithiocarbamate, benzyl-N,N-di(2-hydroxyyethyl)dithiocarbamate, benzyl-N-methyl-N-(2-hydroxyethyl)dithiocarbamate, benzyl-N-methyl-N-carboxymethyldithiocarbamate, di(benzylester) of benzyl-N,N-di(carboxymethyl)dithiocarbamate.

This list is not restrictive, the chemical functionalities (F1) of the initiator may also be added by any other compound capable of forming radicals for initiating the polymerization.

The initiator may also comprise at least a second chemical functionality (F2) allowing to establish a weak, coordinate and/or covalent bond between said initiator and the imprinting molecule or entity.

This functionality (F2) may thus ensure a reversible or an irreversible bond between the molecularly imprinted polymer(s) and the imprinting molecule or entity.

When a substrate is added, particularly a soluble or insoluble solid substrate, or a liquid substrate in step a), this second functionality (F2) may also establish a weak, coordinate and/or covalent bond between the initiator and said substrate.

This second chemical functionality (F2) may be selected from the group comprising hydroxyl, carboxylic ester, thioester, amide, amine, thiol, ether, amidine, guanidine, urea, thiourea, aldehyde, ketone, alkyl, phenyl, benzyl, iminodiacetic acid, nitrilotriacetic acid, ethylene diamine acetic acid, metal chelate in particular Cu-Iminodiacetic acid, Co-iminodiacetic acid, Ni-iminodiacetic acid, Zn-iminodiacetic acid, Ni-nitrilotriacetic acid.

Preferably, chemical functionalities of the initiator are carboxylic acid, benzamidine.

According to a first alternative, said method implements the attachment of the polymerization initiator on a substrate in a sufficiently dense manner. Thus, a film which is uniform and homogenous in thickness is obtained, the thickness being variable depending on the polymerization time.

According to a second alternative, said method implements the attachment of the polymerization initiator on a substrate somewhat less densely. Thus, nanostructures or microstructures of uniform and of homogenous distribution dimensions attached on a substrate are obtained. In this manner, a "structured" product is obtained, making it possible to meet the various requests of interest to the different branches of the industry using this type of product. This has as advantage to allow to manufacture structures which optimize the transduction of a sensor while increasing the specific surface of the MIP.

According to a third alternative, said method implements the usage of the polymerization initiator in a solution with the monomers and the imprinting molecule or entity. Thus, molecularly imprinted polymer(s) are obtained in the form of spherical or non spherical particles of a size ranging between 10 nm and 100 μm, or soluble nanogels of a size less than 1 μm.

In a fourth alternative of the invention, said method advantageously implements the usage of an initiator having one or several additional chemical functionalities for forming covalent or non-covalent bonds with the imprinting molecule or entity. Accordingly, the polymerization initiator at the same time plays the role of a binding monomer, and the polymer chains form based on the imprinting molecule or entity and thus, in a localized manner. The imprinting molecule or entity is thereby completely or partially coated by a sufficiently dense polymer (MIP). According to this alternative, the polymerization initiator is in a solution with the monomers and the imprinting molecule or entity.

In step a), the initiator may be in a mixture with a sensitizing compound selected from the group comprising:

acridines particularly Acriflavine® or Acridine Orange®, phenazines in particular Safranin O®, oxazines, thiazines particularly Methylene Blue or thionine, xanthenes in particular Eosin Y®, Rose Bengal® or Erythrosine®, rhodamines, thioxanthenes, polymethines;

derivatives of thioxanthene particularly isopropylthioxanthone or chlorothioxanthone, coumarins or their derivatives particularly ketocoumarins.

Advantageously, the contact of step a) is done in the presence of at least a pore-forming agent able to form pores in the molecularly imprinted polymer(s) (MIP) that one wishes to obtain, preferably by adding a solvent or a mixture of pore-forming solvent(s), or even by adding a pore-forming agent to a solvent in a solution where there are reactive substances.

Thus, molecularly imprinted polymer(s) of porous structure are obtained, thereby facilitating the access to and/or the starting point of imprinting molecules or entities of polymer (MIP).

Preferably, the method according to the present invention implements at least a pore-forming agent giving the polymer (MIP) a porous structure whereof the diameter of the pores ranges between 0.1 nm and 10 µm, and preferably between 1 nm and 1 µm. More preferentially, the pore-forming solvent may be an organic or non organic aqueous or non-aqueous solvent. Preferably, the contact of step a) is done in the presence of at least a pore-forming solvent selected from the group comprising benzene, toluene, xylene, chlorinated solvents particularly chloroform, dichloromethane, dichloroethane, and 1,1,2,2,-tetrachloroethane, and/or perfluorinated solvents, particularly hexafluorocyclohexane, ethers particularly tetrahydrofuran, diethylene glycol dimethyl ether and triethylene glycol dimethyl ether, amides in particular dimethylformamide and formamide, nitriles particularly acetonitrile and caprylonitrile, ketones particularly acetone, esters particularly ethyl acetate, alkanes, in particular hexane and heptanes, alcohols particularly methanol, ethanol, isopropanol, butanol, decanol, water, or a mixture of these.

The aforementioned solvent(s) may further, comprise(s) a pore-forming agent particularly of polymeric nature or other, preferably, a linear polymer soluble in said solvent, particularly polyethylene glycol, polyvinyl alcohol, polyvinyl acetate, polystyrene, polymethylmethacrylate. The function of this agent is to induce and accelerate pore formation. Such agents are also described in the document [8], which is incorporated by reference.

As previously indicated, in step b) a polymerization under exposure to light irradiation of visible or UV wavelength or with supply of thermal energy is performed to form molecularly imprinted polymer(s) (MIP) over or around said imprinting molecule or entity.

According to another feature, in step b) the method according to the invention implements radiations or light irradiation in the form of a ray or beam of light rays of visible or UV wavelength.

Thus, in step b) a polymerization under exposure to light irradiation of visible or UV wavelength ranging between 100 nm and 1200 nm is carried out. The wavelength preferably ranges between 150 nm and 750 nm, and more preferentially between 250 nm and 550 nm.

According to another feature, in step b) the polymerization is implemented by a supply of thermal energy which allows for the activation of the polymerization initiator. This may be done for example by placing the polymerization mixture in a thermostated enclosure whereof the temperature is adjustable.

Thus, the polymerization may be done in step b) with a supply of thermal energy at a temperature ranging between 0° C. and 200° C. Preferably, the temperature ranges between 25° C. and 100° C., and more preferentially between 40° C. and 70° C.

Preferably, the polymerization is done without chemically modifying the imprinting molecules or entities.

As previously mentioned, in step c) of the method according to the invention, non polymerized monomer or monomers and/or all or part of the imprinting molecule or entity of the polymer formed in b) are removed with a solvent or a convenient mixture of solvent or solvents.

The solvent may be selected from the group comprising, water, methanol, ethanol, isopropanol, acetonitrile, chloroform, heptane, toluene, acetic acid, or their mixture, or supercritical $CO_2$. Preferably, the solvent is a mixture of methanol and acetic acid.

Apart from the indicated solvents, the imprinting molecule or entity may also be removed from the polymer formed in b) with another agent or another treatment liable to facilitate the removal of the imprinting molecule or entity.

According to an alternative of the invention, in step c), apart from the solvent or mixture of solvents, the imprinting molecule or entity may be removed from the polymer formed in b) with a solvent or a mixture of solvents containing another agent selected from the group comprising:

a detergent particularly sodium dodecyl sulfate, cetyltrimethylammonium bromide, Triton X-100, Empigen BB®;

urea;

trifluoroacetic acid;

triethylamine;

hydrolytic enzyme selected from the group comprising a peptidase or a protease, particularly trypsin or proteinase K;

nuclease, particularly nuclease of *Staphylococcus aureus* or ribonuclease A;

lipase, particularly porcine pancreatic lipase or lipase XIII of *Pseudomonas* sp.;

glycosidase, particularly beta-glucosidase, alpha glucosidase, or beta galactosidase;

a salt particularly sodium thiosulfate.

The skilled person recognizes the appropriate solvent(s) and, if necessary, the agent, particularly among those mentioned previously, to achieve step c) wherein the non polymerized monomers and/or all or part of the imprinting molecule or entity of the polymer formed in b) are removed.

According to another alternative of the present invention, apart from the solvent, the imprinting molecule or entity of the polymer formed in b) is removed by applying an electric field preferably ranging between 1 V/cm and 100 V/cm. In this alternative, the polymer (MIP) is retained by a semipermeable membrane which the imprinting molecule or entity may cross.

The present invention also relates to a molecularly imprinted polymer(s) (MIP) liable to be obtained by the method of the present invention.

The molecularly imprinted polymer(s) (MIP) liable to be obtained by the implementation of the method according to the present invention may come in the form of a film with a thickness ranging between 1 nm and 100 µm, preferably in the form of a film of constant or substantially constant thickness.

It may also come in the form of a spatially structured film, preferably having geometric units whereof the diameters or lateral dimensions range between 1 nm and 10 µm.

Said polymer may also come in the form of spherical particles particularly in the form of spherical microbeads or nanobeads in suspension, or microgels or nanogels in a solution, whereof the diameter preferably ranges between 1 nm and 100 µm.

The molecularly imprinted polymer(s) (MIP) liable to be obtained according to the method of the present invention, may have a porous structure whereof the diameter of the pores ranges between 0.1 nm and 10 µm.

Another object of the present invention is the use of a polymer liable to be obtained by the method of the invention within the realization of biomimetic biosensors, biomimetic biochips, chemical sensors, specific adsorption separation devices, as a coating, in particular, for salting out active products.

More particularly, the present invention relates to the usage of (a) molecularly imprinted polymer(s) obtained by the implementation of the method according to the invention for making a qualitative and/or quantitative detector of the presence of at least an entity or target molecule in the sample to analyze as well as the detector obtained by the implementation of the method according to the invention.

The present invention also relates to (a) molecularly imprinted polymer(s) obtained by the implementation of the method according to the present invention for making a reversible sensor of at least an entity or target molecule as well as the reversible sensor obtained by implementing the method according to the present invention.

Finally, the present invention relates to the usage of (a) molecularly imprinted polymer(s) obtained by the implementation of the method according to the present invention for making an affinity separation device for at least an entity or target molecule as well as the affinity separation device obtained by the implementation of the method according to the present invention.

The present invention makes it possible to resolve the issue of the shaping, as well as the morphology and inner structure, of materials or molecularly imprinted polymer(s) (MIP) with the aim of particularly manufacturing chemical sensors in the aforementioned sense whereof the functioning rests on the principle of molecular recognition.

The MIP preparation process also makes it possible to obtain a multi-scale structuring, such as a simultaneous micro-structuring and nanostructuring. The method also makes it possible to obtain a multiple nanostructuring or a multiple microstructuring, such as a superposition of several MIP films on a surface, or spherical or semi-spherical structures of core-shell or core-multishell type.

This makes it possible to optimize at the same time the recognition selectivity and the response sensitivity of a device based on such a material (MIP) that is nanostructured on two scales. This also makes it possible to optimize the properties of the material, or to incorporate entities serving for its specific physico-chemical identification.

The present invention also relates to initiators of formulas D1 (FIG. 2), D2 and D6 (FIG. 4), D3 (FIG. 9), D4 (FIG. 13), D5 (FIG. 14) as well as their usage for preparing (a) molecularly imprinted polymer(s) through radical polymerization.

Other advantages may still become apparent to the skilled person upon reading the examples below, which are illustrated by the accompanying drawings.

EXAMPLES

In the examples, one of the imprinting molecules used as a specimen to demonstrate the printing of the polymeric material is S-propranolol (beta-blocking). The importance of this molecule lies, inter alia, in its chirality: if one of the enantiomers is used to generate the imprint, the other forms an excellent control for the polymer's selectivity (MIP). Another imprinting molecule used is trypsin. The importance of the trypsin is that it is a protein which is a considerably bigger molecule than the S-propranolol.

The selectivity of the synthesized crude polymers for a given molecule can be characterized by different means: the use of fluorescent or radioactive labels (balance tests), liquid chromatography, or by spectroscopic methods based on fluorescence, visible or IR ultraviolet light absorption, or on the Raman scattering.

It has been validated that the method according to the present invention is extendable to other polymerizable mixtures compatible with the molecular printing technique. The thickness of a film and, if need be, the lateral dimension of the polymers' micro- or nanostructures, and the diameter of the produced MIP spherical micro/nanoshells are directly linked to the irradiation time and to the power of the used beam, or to the heating time for the priming by thermal power supply. In these conditions, these dimensions can be easily fixed between a few nm and a few µm.

Example 1: Polymerization Multi-Initiators According to the Invention

Figure 1:
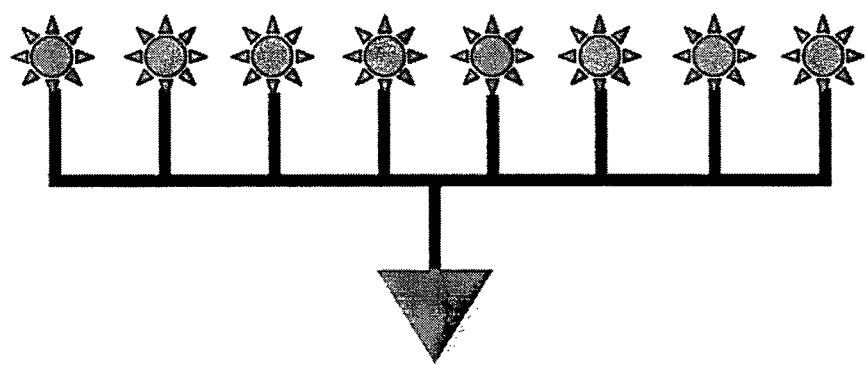
FIG. 1 represents a simplified illustration of the general structure of the initiators of photo or thermosensitive polymerization of the present invention.

FIG. 1 illustrates a schematic representation of the polymerization multi-initiator which also has a functionality enabling it to be attached to a substrate or to the imprinting molecule or entity.

Figure 2:
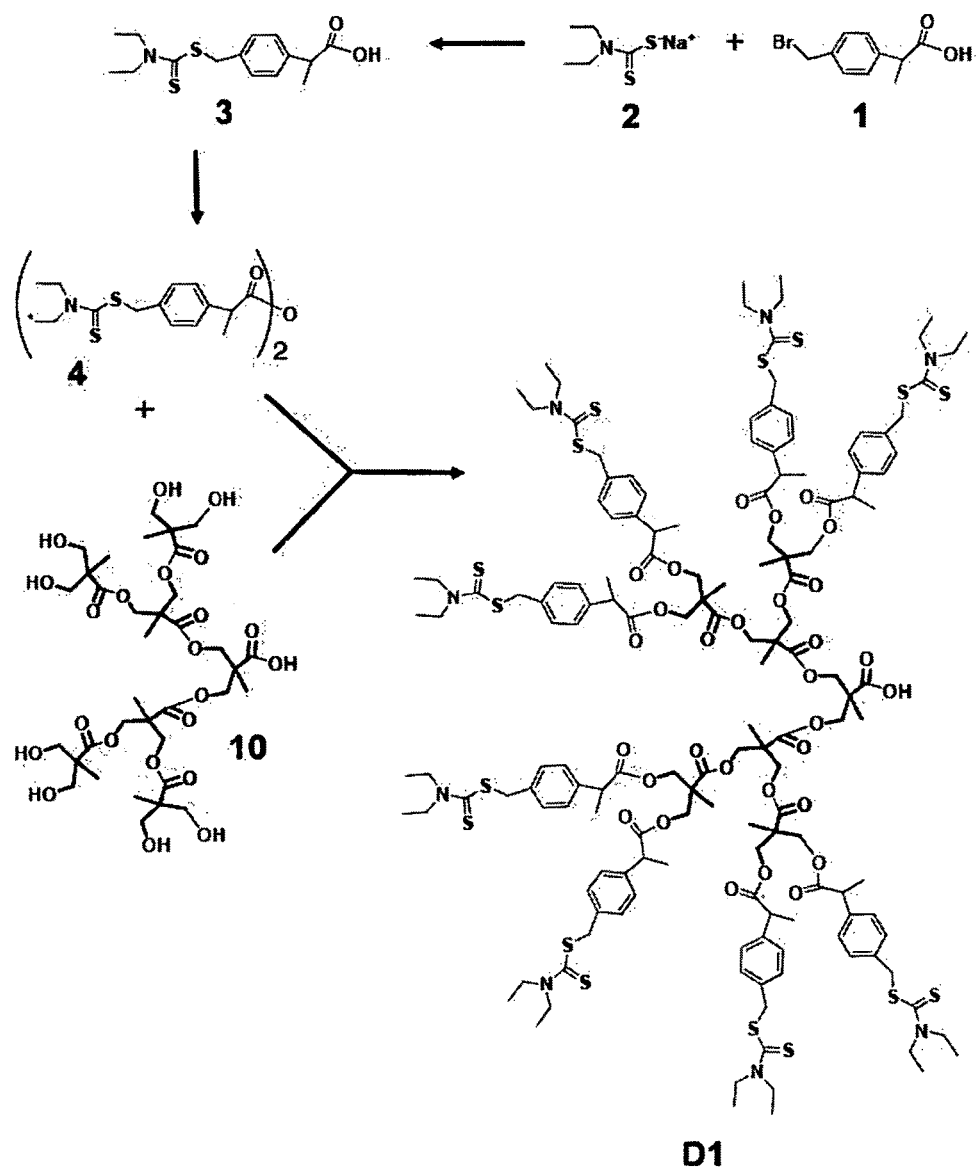
FIG. 2 represents the chemical structure and the chemical synthesis of molecule D1, the specific initiator molecule described in example 1. D1 is synthesized on the basis of a dendritic structure wherein the functionality (F2) at the core allowing for the formation of covalent or non-covalent bonds is a carboxyl function, and wherein the functionalities (F1) at the periphery allow to generate reactive radicals and hence to initiate a radical polymerization are 8 benzyl diethyldithiocarbamate functions (iniferter type initiator for living radical polymerization).

1.1. Initiator D1:

An embodiment of a multi-initiator is the molecule D1 described in FIG. 2. This molecule is based on a dendritic structure (generation 3 dendron), comprising at the core a functionality (F2) which is a —COOH functionality allowing to couple or attach, by covalent or non-covalent bonds (hydrogen or ion bonds), the molecule on a substrate, a surface, the imprinting molecule or entity, and containing on its periphery iniferter-type living radical polymerization initiators (benzyl diethyldithiocarbamate).

Synthesis of Molecule D1:

The synthesis phases, the used reagents and the structure of the obtained molecule D1 are illustrated in FIG. 2.

The molecule 1 (1 equivalent, 1 mmol, Sigma-Aldrich 530360) and the molecule 2 (1.2 equivalents, 1.2 mmol, Sigma-Aldrich 228680) are dissolved in 20 ml of tetrahydrofuran (THF) under a nitrogen atmosphere. The reaction evolves for 4 hours under agitation at 70° C. under nitrogen atmosphere. The organic phase is washed with saturated sodium chloride solution, dried over magnesium sulphate and concentrated. A chromatography of the residue on silica gel allows to isolate the expected product 3. The molecule 3 (0.9 mmol) is reacted with N, N-dicyclohexylcarbodiimide (1.5 equivalent, 1.8 mmol, Sigma-Aldrich 36650) in dichloromethane (15 ml) at 25° C. for 2 hours. A precipitate is formed and is eliminated by filtering on sintered glass. The filtrate is then concentrated on the rotary evaporator to produce anhydride 4. In the presence of 4-(dimethylamino) pyridine (0.2 equivalents/—OH, 1.3 mmol) and pyridine (5 equivalents/—OH, 32 mmol), the molecule 4 (9.6 equivalents, 7.7 mmol, 1.5 equivalents/—OH) and the dendron 10 (1 equivalent, 0.8 mmol, Polymer Factory PFd-G3-COOH—OH) are dissolved in dichloromethane (20 ml). The reaction evolves at 25° C. for 24 hours. The organic phase is rinsed with a sodium carbonate aqueous solution 10% and a sodium carbonate saturated solution, dried over magnesium sulphate, filtered, then concentrated under reduced pressure to produce oil. Said oil is purified with chromatography on silica gel (heptanes, ethyl acetate 40/60) to isolate dendron D1 (0.4 mmol) with an overall yield of 40%.

Figure 4:
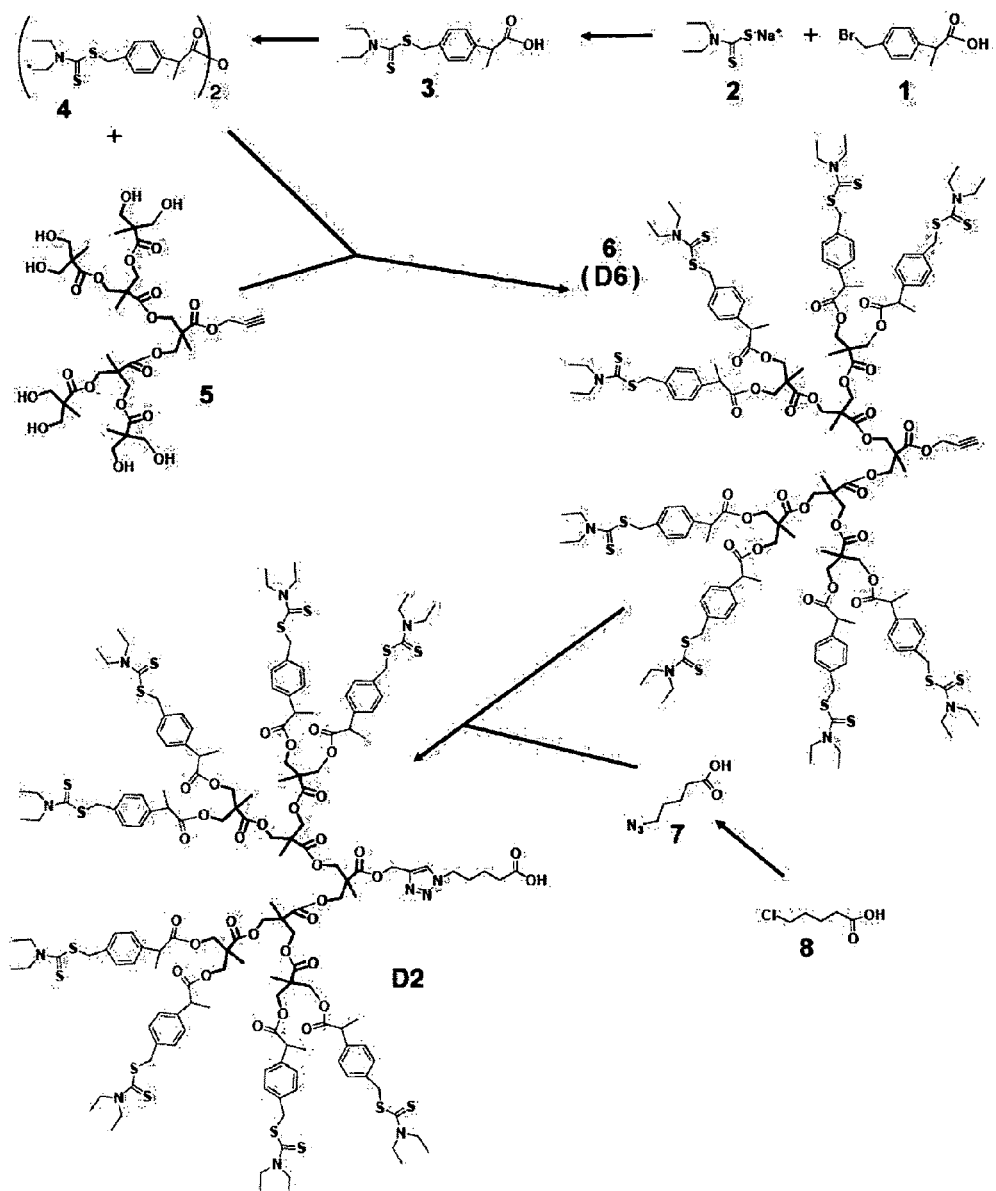
FIG. 4 represents the chemical structure and the chemical synthesis of molecule D2, the specific initiator molecule used in example 2, as well as that of molecule D6 (also identified as 6). D2 is synthesized on the basis of a dendritic structure wherein the functionality (F2) at the core allowing for the formation of a covalent or non-covalent bond attached to the dendron (generation 3) is a carboxyl function, and wherein functionalities (F1) at the periphery allow to generate reactive radicals and hence to initiate a radical polymerization are 8 benzyl diethyldithiocarbamate functions (iniferter type initiator for living radical polymerization). Molecule 6 or D6 is synthesized on the basis of dendritic structure wherein the functionality (F2) at the core is an acetylene function allowing for a click chemistry attachment on another entity comprising an azide group, and wherein the 8 functionalities (F1) at the periphery are benzyl diethyldithiocarbamate functionalities allowing to generate reactive radicals, and hence to initiate a radical polymerization.

1.2. Initiators D2 and D6:

Another embodiment of multi-initiator is the molecule D2 the structure of which is described in FIG. 4. This molecule is based on a dendritic structure (generation 3 dendron), comprising:
- at the core a functionality (F2) which is a carboxylic acid functionality allowing an attachment by covalent or non-covalent binding and tied to the dendron via a spacer, and
- at the periphery 8 functionalities (F1) which are benzyl diethyldithiocarbamate functionalities allowing to generate reactive radicals, and therefore to initiate a radical polymerization (iniferter-type initiator for living radical polymerization).

Molecule D6 (also identified as 6) the structure of which is described in FIG. 4 is another embodiment of a multi-initiator. This molecule is based on a dendritic structure (generation 3 dendron), comprising at the core a functionality (F2) which is an acetylene functionality allowing a binding by "click chemistry" on another entity comprising an azide group. As in D2, in the molecule 6 or D6, the functionalities (F1) which are at the periphery, are benzyldiethyldithiocarbamate functionalities allowing to generate active radicals, and therefore to initiate a radical polymerization.

The click chemistry enables to develop a series of strong, reproducible, selective and adjustable reactions. The main click reactions consist in forming energetically favorable carbon-heteroatom bindings [11, 12].

The synthesis phases, the used reagents and the structure of the obtained molecules D2 and 6 or D6 are illustrated in FIG. 4.

The preparation of molecules 3 and 4 is achieved according to the protocol described by initiator D1. To a solution of the molecule 4 (9.6 equivalents, 7.7 mmol, 1.5 equivalents/—OH) in dichloromethane (20 ml) is added the Dendron 5 (1 equivalent, 0.8 mmol, Polymer Factory PFd-G3-Acetylene-OH) and a solution of 4-dimethylaminopyridin (0.2 equivalents/—OH, 1.3 mmol) in the pyridine (5 equivalents/OH, 32 mmol). The reaction evolves at 25° C. for 24 hours. The organic phase is washed with a sodium carbonate aqueous solution 10% and with a saturated sodium chloride solution, dried over magnesium sulphate then concentrated. A chromatography on silica gel (heptanes/ethyl acetate) allows to isolate the molecule 6 or D6 (0.3 mmol). As intermediate for synthesis, molecule 7 is prepared from molecule 8 (1 equivalent, 0.5 mmol) by reacting said molecule with sodium azide (1.3 equivalent, 0.65 mmol) in dimethyl sulfoxide (5 ml) by microwave irradiation for 30 minutes at 120° C. [9]. To a solution of molecule 6 or D6 (1 equivalent, 0.3 mmol) in a mixture of tetrahydrofuran/water ½ (10 ml) is added 1.2 equivalents of the molecule 7 (0.4 mmol) in the presence of $CuSO_4$ and of 0.3 equivalents of sodium ascorbate. The reaction is carried out at 25° C. for 24 h. The molecule D2 is then purified by chromatography on silica gel and is obtained with an overall yield of 12% (0.2 mmol).

Figure 5A:
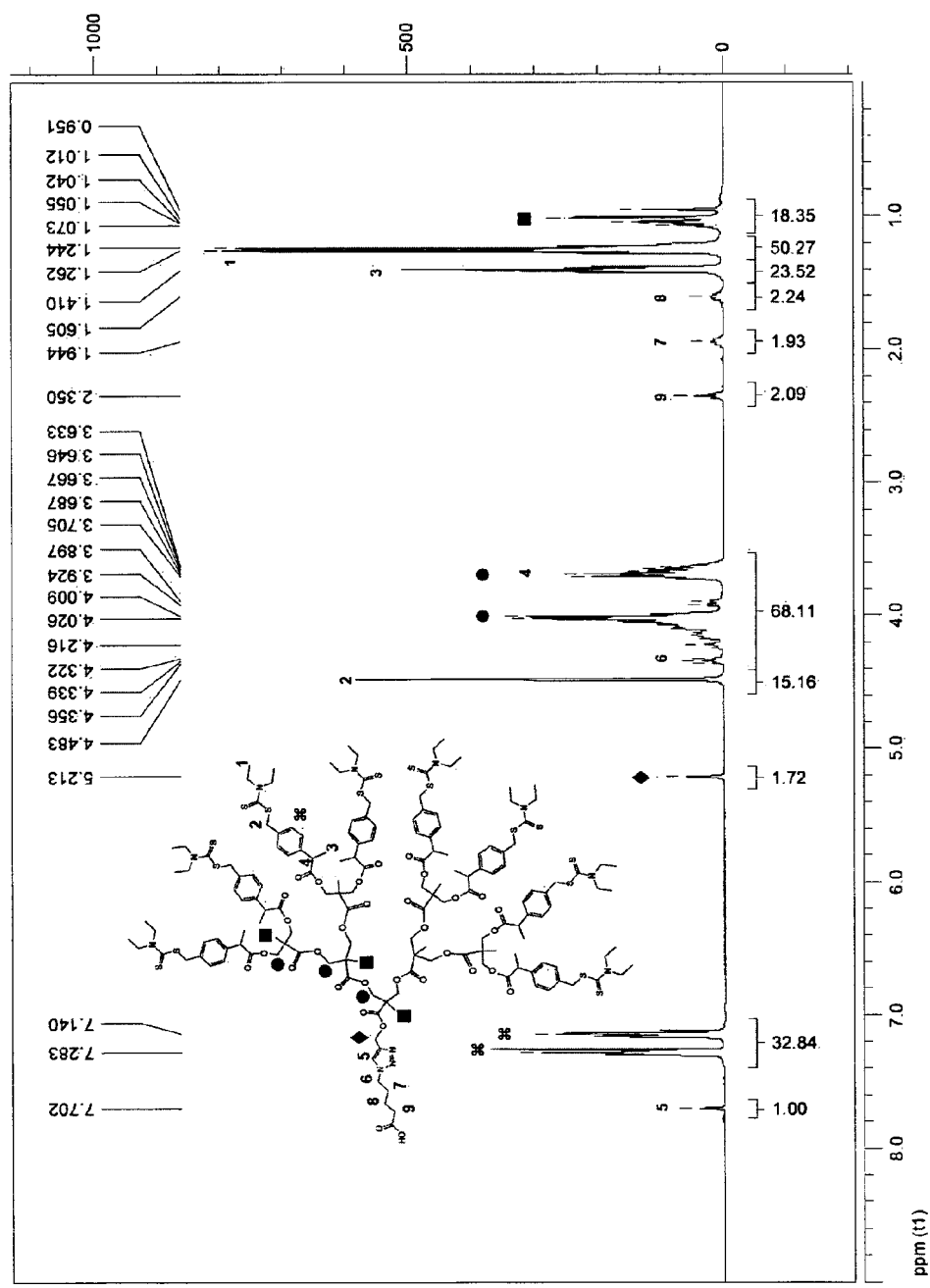
FIGS. 5A and 5B illustrate the proton (FIG. 5A) and carbon (FIG. 5B) nuclear magnetic resonance (NMR) spectra of D2.
Figure 5B:
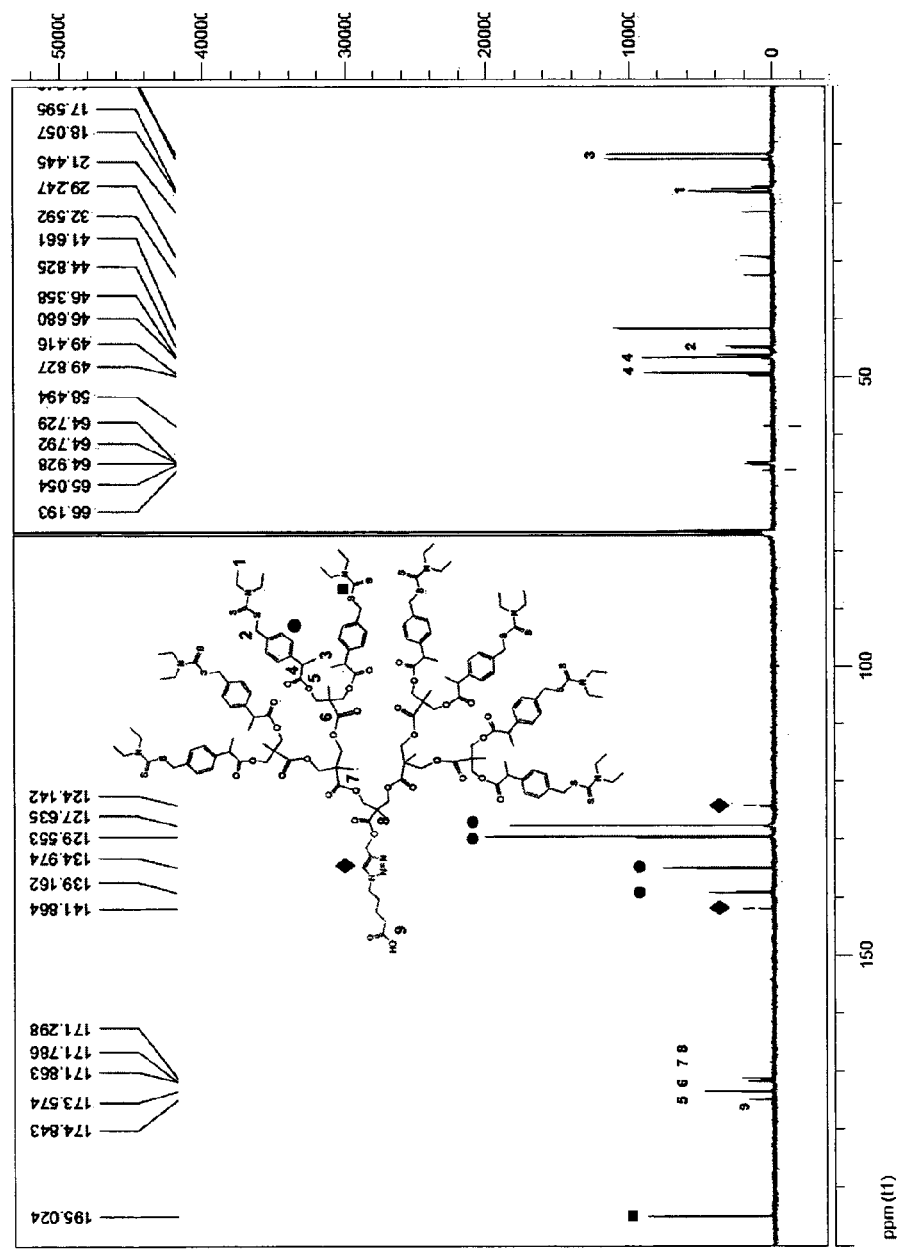

The proton and carbon nuclear magnetic resonance spectra (RMN) of the molecule D2 are illustrated in FIG. 5.

1.3. D3 Initiator:

Molecule D3 Synthesis:

The molecule D2 (1 equivalent, 0.2 mmol) is allowed to react with 1 equivalent of the molecule 9 in the presence of 0.2 equivalents of 4-dimethylaminopyridine and of 1.2 equivalents of N,N-dicyclohexylcarbodiimide in dichloromethane (10 ml) to form the molecule D3 which is purified by column chromatography.

The molecule 9 is commercially available.

Figure 9:
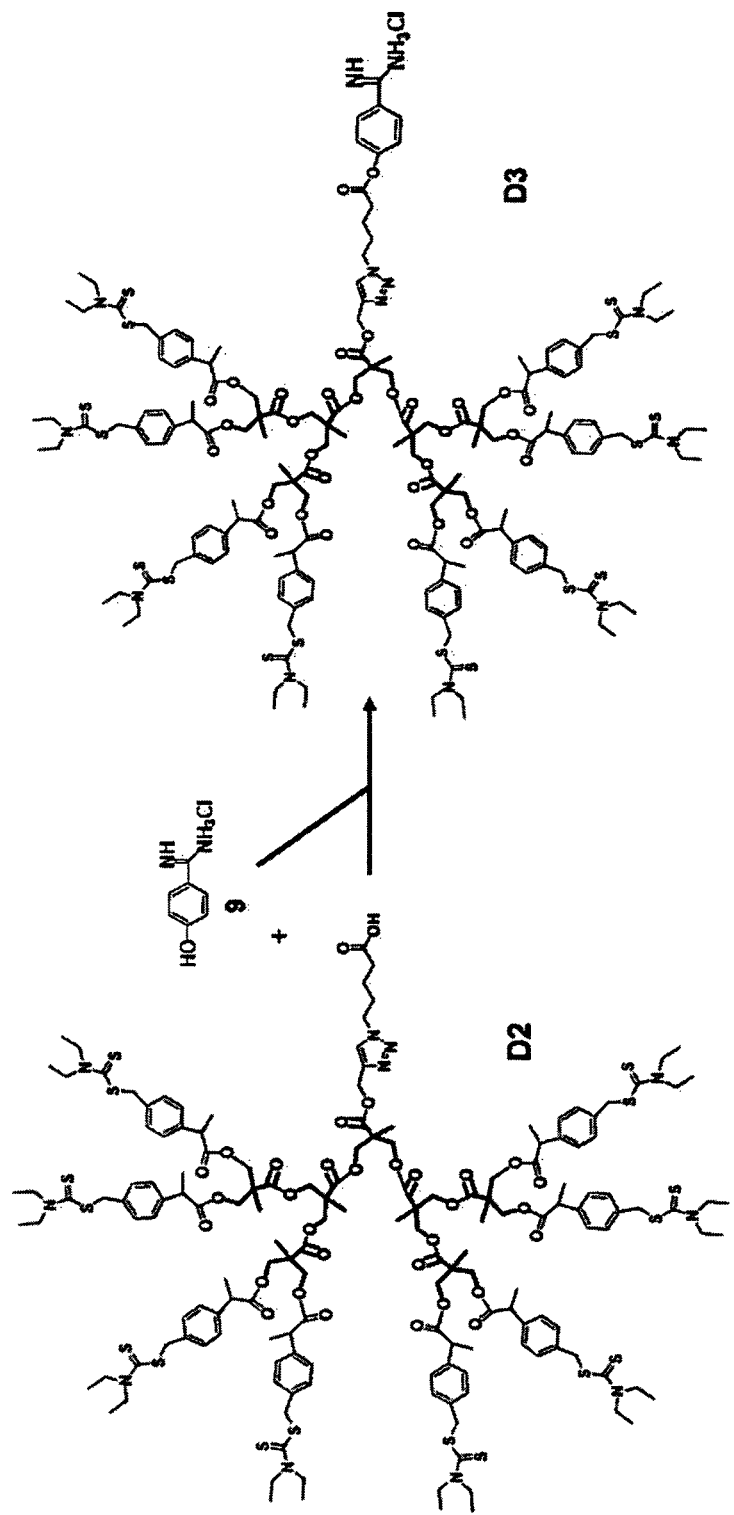
FIG. 9 illustrates the chemical structure and the synthesis pathway of molecule D3, specific initiator molecule used in example 3. D3 is synthesized on the basis of a dendritic structure (generation 3 dendron) wherein the core function (F2) allowing a coupling by covalent or non-covalent bonds is a benzamidine functionality attached to the dendron via a spacer, and wherein functionalities (F1) at the periphery allowing to generate reactive radicals, and therefore to initiate a radical polymerization, are 8 benzyl dimethyldithio-carbamate functionalities (iniferter-type initiator for living radical polymerization).

FIG. 9 illustrates the structure of the polymerization initiator used in this example, the molecule D3, and its synthesis pathway from D2.

Figure 10:
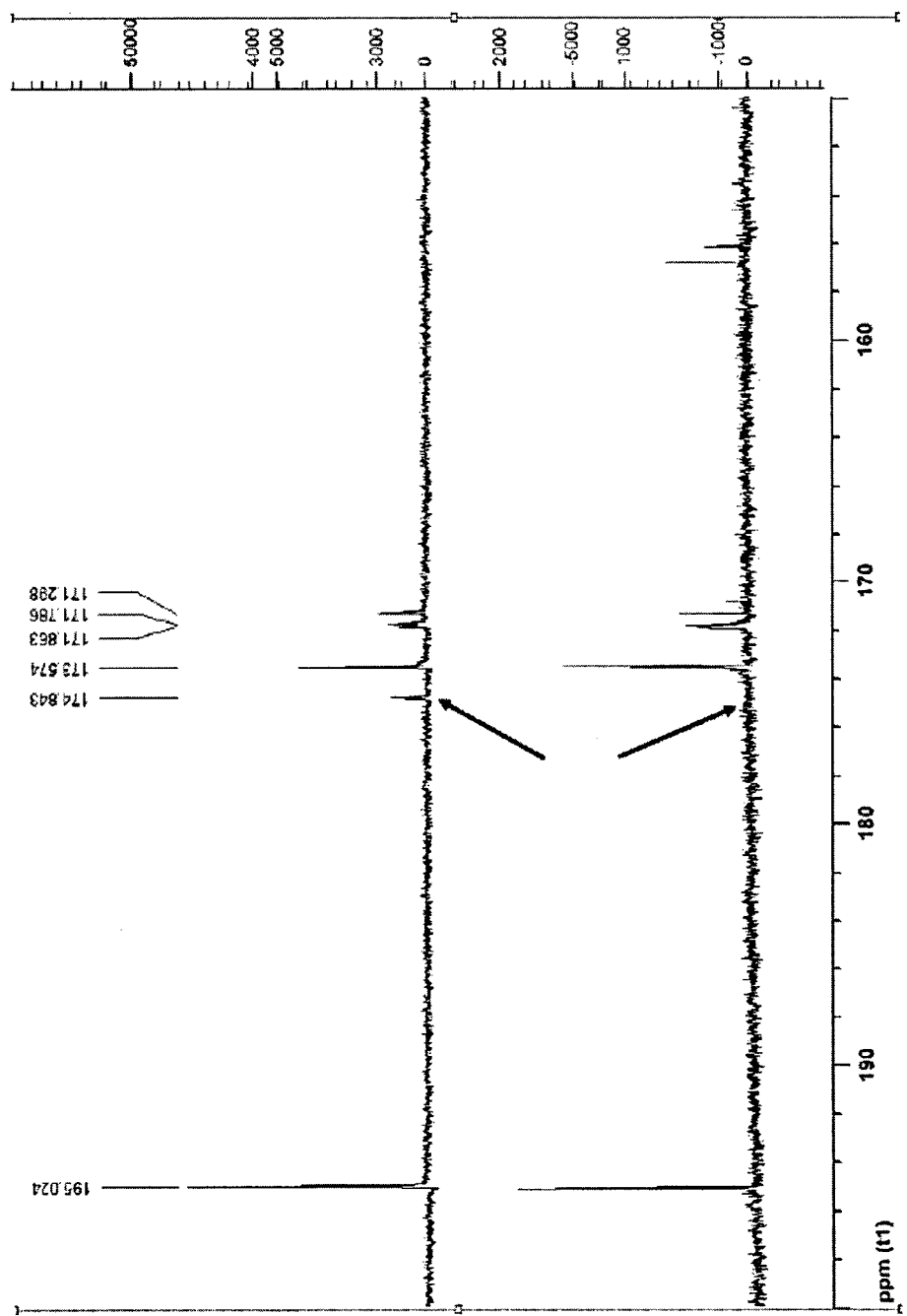
FIG. 10 shows the carbon nuclear magnetic resonance spectra of D3 (at the bottom) and, for comparison purpose, the carbon nuclear magnetic resonance spectra of D2 before coupling with compound 9 (at the top). The arrows indicate the disappearance of the signal of the functionality —COOH free after the coupling of D2 with the compound 9.

FIG. 10 illustrates the carbon nuclear magnetic resonance spectrum of D3 (bottom spectrum). The carbon nuclear magnetic resonance spectrum of D2 before coupling with component 9 is also given for comparative purpose (top spectrum). The arrows demonstrate that the signal corresponding to the free —COOH functionality disappears in D3, signal which is present in D2 before coupling with component 9.

Figure 13:
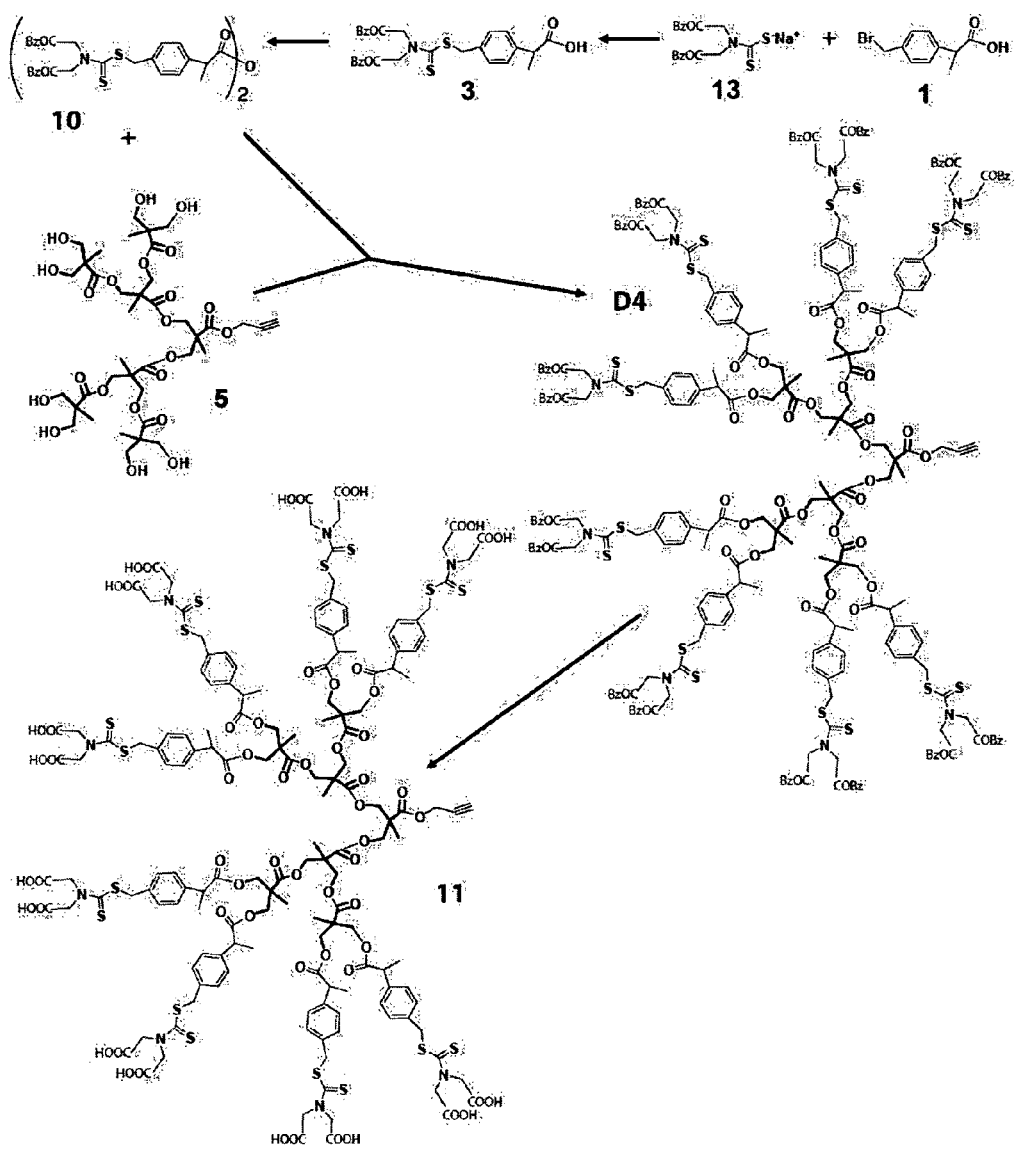
FIG. 13 illustrates the chemical structure and the synthesis pathway of the molecule D4, the specific initiator molecule described in example 1. D4 is synthesized on the basis of a dendritic structure wherein the functionalities (F1) at the periphery allowing to generate reactive radicals and therefore to initiate a radical polymerization, are 8 benzyl-N,N- di(carboxymethyl)dithiocarbamate di(benzyl ester) functionalities (iniferter-type initiator for living radical polymerization). From the molecule D4, the molecule 11 is obtainable by catalytic hydrogenolysis of the benzyl ester functionalities.

1.4. Initiator D4:

Another embodiment of a multi-initiator is the molecule D4 the structure of which is described in FIG. 13. This molecule is based on a dendritic structure (generation 3 Dendron), comprising:
- at the core a functionality (F2) which is an acetylene functionality allowing the binding by "click chemistry" on another entity comprising an azide grouping, and
- at the periphery, 8 functionalities (F1) which are benzyl diethyldithiocarbamate di(benzyl ester) functionalities allowing to generate reactive radicals, and therefore to initiate a radical polymerization (iniferter-type initiator for living radical polymerization).

Molecule D4 Synthesis:

The synthesis phases, the used reagents and the structure of the obtained D4 molecule are illustrated in FIG. 13.

The molecule 1 (1 equivalent, 1 mmol, Sigma-Aldrich 530360) and the molecule 13 (1.2 equivalents, 1.2 mmol) are dissolved in 20 ml of tetrahydrofuran (THF) under nitrogen atmosphere (the molecule 13 is obtained from ammonium N,N-di(carboxymethyl)dithiocarbamate, synthesized in advance according to G. R. Gale et al., Ann. Clin. Lab. Sci. 1983, 13, 474-481 [10] (which is incorporated herein by reference), which is later esterified with benzyl alcohol). The reaction develops for 4 hours under agitation at 70° C. under nitrogen atmosphere. The organic phase is washed with a saturated sodium chloride solution, dried on magnesium sulphate and concentrated. A chromatography of the residue on silica gel enables to isolate the desired product 3. The molecule 3 (0.9 mmol) is reacted with N, N-dicyclohexylcarbodiimide (1.5 equivalent, 1.8 mmol, Sigma-Aldrich 36650) in the dichloromethane (15 ml) at 25° C. for 2 hours. A precipitate is formed and eliminated by filtration on sintered glass. The filtrate is then concentrated on the rotary evaporator to produce anhydride 4. To a solution of the molecule 10 (9.6 equivalents, 7.7 mmol, 1, equivalents/—OH) in dichloromethane (20 ml) is added the dendron 5 (1 equivalent, 0.8 mmol, Polymer Factory PFd-G3-Acetylene-OH) and a solution of 4-dimethylaminopyridine (0.2 equivalents/—OH, 1.3 mmol) in the pyridine (5 equivalents/—OH, 32 mmol). The reaction evolves at 25° C. for 24 hours. The organic phase is washed with an aqueous solution of sodium carbonate, dried on magnesium sulphate then concentrated. A chromatography on silica gel (heptanes/ethyl acetate) enables to isolate the molecule D4 (0.3 mmol). The molecule D4 is then purified by chromatography on silica gel and is obtained with an overall yield of 13% (0.2 mmol).

From the molecule D4, the molecule 11 is obtainable by catalytic hydrogenolysis of benzyl ester functionalities at the periphery of D4.

1.5. Initiator D5:

An embodiment of a multi-initiator is the molecule D5 described in FIG. 14. This molecule is based on a dendritic structure (generation 3 dendron), comprising at the core a functionality (F2) which is a benzyl carboxylate functionality (—COBz, and containing on its periphery functionalities (F1) of iniferter-type living radical polymerization initiators (benzyl diethyldithiocarbamate).

Molecule D5 Synthesis:

The synthesis phases, the used reagents and the structure of the D5 molecule are illustrated in FIG. 14.

The molecule 1 (1 equivalent, 1 mmol, Sigma-Aldrich 530360) and the molecule 2 (1.2 equivalents, 1.2 mmol, Sigma-Aldrich 228680) are dissolved in 20 ml of tetrahydrofuran (THF) under nitrogen atmosphere. The reaction evolves for 4 hours under agitation at 70° C. under nitrogen atmosphere. The organic phase is washed with a saturated sodium chloride solution, dried on magnesium sulphate and concentrated. A chromatology of the residue on silica gel allows to isolate the desired product 3. The molecule 3 (0.9 mmol) is reacted with N, N-dicyclohexylcarbodiimide (1.5 equivalent, 1.8 mmol, Sigma-Aldrich 36650) in dichloromethane (15 ml) at 25° C. for 2 hours. A precipitate is formed and is eliminated by filtration on sintered glass. The filtrate is then concentrated at the rotary evaporator to produce anhydride 4. In the presence of 4-(dimethylamino) pyridine (0.2 equivalents/—OH, 1.3 mmol) of pyridine (5 equivalents/—OH) and the Dendron 12 (1 equivalent, 0.8 mmol, Polymer Factory PFd-G3-COBz-OH) are dissolved in dichloromethane (20 ml). The reaction evolves at 25° C. for 48 hours to produce the molecule D5, which is purified by chromatography on silica gel (heptanes/ethyl acetate 40/60), with an overall yield of 40%.

The proton and carbon nuclear magnetic resonance (NMR) spectra of the molecule D5 are illustrated in FIGS. 15A and 15B.

Example 2: Molecularly Imprinted Polymer (MIP) and Preparation Process According to the Invention from Initiator D2

Figure 3:
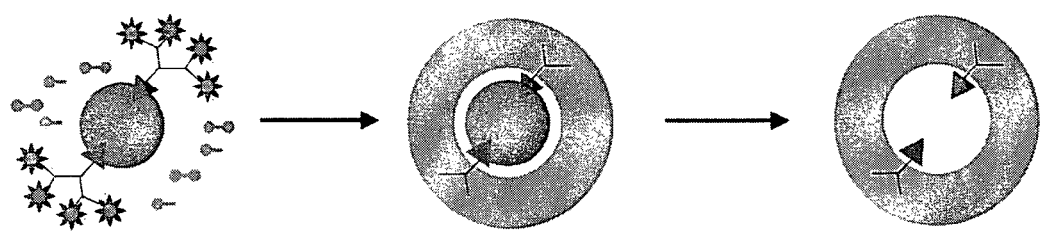
FIG. 3 represents a simplified illustration of the preparation of polymers (MIP) in a solution or a suspension according to the invention (example 2).

This embodiment describes the synthesis of the molecularly imprinted polymer (MIP) for the S-propranolol target molecule by using initiator D2. D2 is capable of establishing links with S-propranolol, the latter acting as an imprinting molecule. The method is schematically represented in FIG. 3.

MIP Synthesis

TABLE 1

Formulations and reagents

| Functionalities | Products | Used quantities |
|---|---|---|
| Imprinting molecule | S-propranolol | 3.0 mg |
| Attaching monomer | None, the initiator acts as a monomer at the same time | — |
| Cross-linked monomer | Ethylene glycol dimethacrylate | 154.0 μl |

TABLE 1-continued

Formulations and reagents

| Functionalities | Products | Used quantities |
|---|---|---|
| Initiator | D2 | 68.6 mg |
| Solvent | Acetonitrile | 3 ml |

A solution A is prepared by weighing 3.0 mg of S-propranolol which is then dissolved in 1.5 ml of acetonitrile, then 154 μl of ethylene glycol dimethacrylate is added. The whole is placed in an ultrasound bath until complete dissolution.

A solution B is prepared similarly by weighing 68.6 mg of D2 which is then dissolved in 1.5 ml of acetonitrile.

The whole is again placed in an ultrasound bath until complete dissolution.

In the dark, solution A is mixed with solution B in a glass test tube of 15 ml, then the tube is closed with a septum cap. The tube is placed on ice for 10 min then argon is introduced into the solution through the septum for 3 min.

The tube is irradiated with a UV lamp of 350 nm for a given time period to polymerize (from 5 min. to 12 hours). The suspended polymer beads obtained are incubated at 25° C. in methanol/acetic acid 4:1 mixtures (three times for 1 h) and in methanol (3 times for 1 h). This treatment allows the releasing of the imprints of the obtained molecularly imprinted polymer.

The evolution of the size of the MIP particles is proportional to the logarithm of the dose of light used to induce the photopolymerization. The diameter is easily adaptable between 30 nm and 3 μm by adjusting exposure time.

MIP Characteristics and Properties

Figure 6:
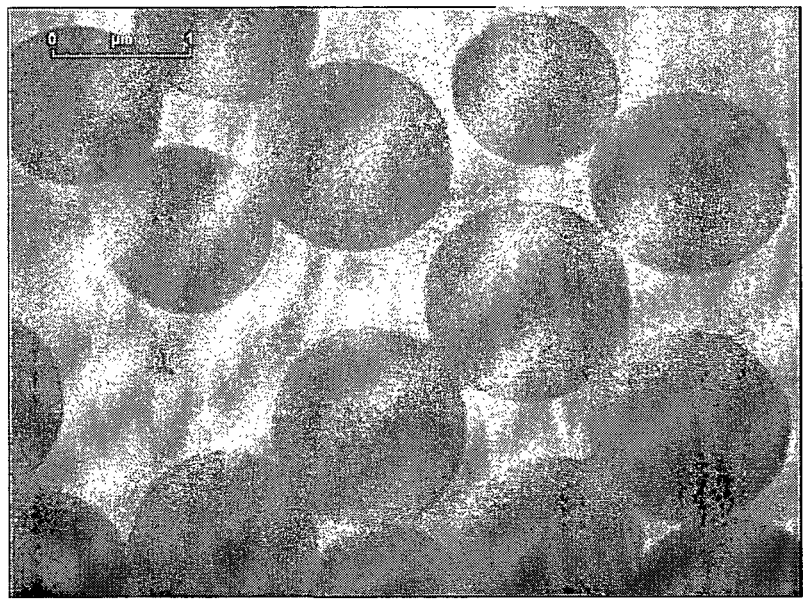
FIG. 6 shows an image taken, using transmission electron microscopy imagery, of MIP particles obtained by the process according to the present invention and according to the drawing of FIG. 3 (at the top), according to example 2; and for comparison purpose, an image taken, using transmission electron microscopy imagery, of MIP particles obtained by means of a polymerization initiator comprising one single functionality capable of producing radicals, benzyl dimethyldithiocarbamate (at the bottom), the total number of dithiocarbamate functionalities being the same in both cases.
Figure 6:
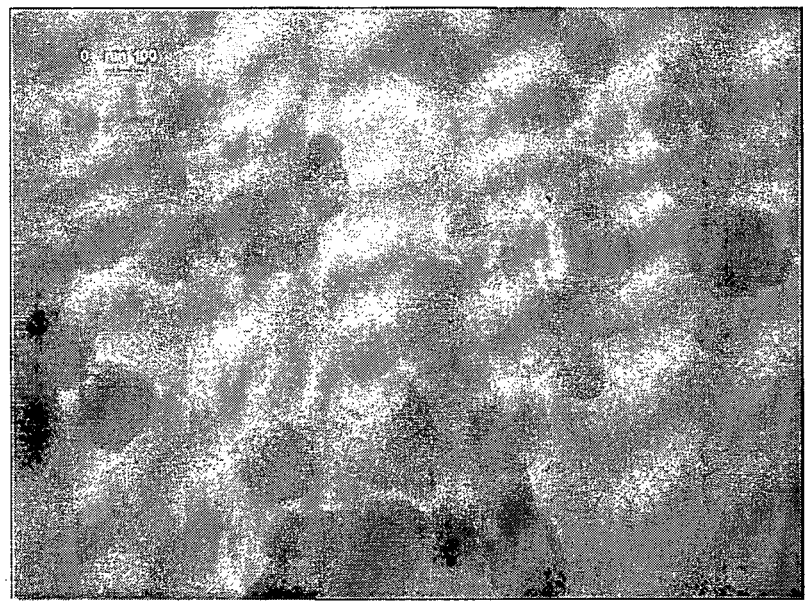

FIG. 6 illustrates an image of MIP spherical particles obtained according to the method of the invention, using transmitting electron microscopy (image at the top). It is noted that by using a multifunctional initiator according to the invention, the formed particles are dense wherein the diameter is of about 1.3 μm. In FIG. 6, the image of the bottom shows MIP particles obtained by a method implementing a multifunctional initiator, benzyl dimethyldithiocarbamate, the total number of dithiocarbamate functionalities being the same in both cases. It is clear that according to the method and particularly according to the used initiator, the resulting MIP do not have the same size, morphology or shape.

In order to assess the molecularly imprinted effect, the MIP and a control polymer chemically identical but synthesized in the absence of S-propranolol are incubated with tritium-labeled propranolol ($^3$H—S-propranolol). To do that, in two series of test tubes of 1.5 ml are introduced, respectively, increasing quantities (from 100 to 900 μg) of MIP and of the control polymer, suspended in acetonitrile comprising 0.5% of acetic acid. 1 pmol of $^3$H—S-propranolol is added to this suspension, then the tubes are incubated under agitation for 2 h at 25° C. After centrifugation, the radioactivity into the supernatant is determined by scintillation counting in liquid phase. The obtained value corresponds to the $^3$H—S-propranolol, not linked to the polymer, and the linked moiety is calculable by the difference between the quantity of $^3$H—S-propranolol found in the supernatant and the total quantity of $^3$H—S-propranolol added to each test tube.

Figure 7:
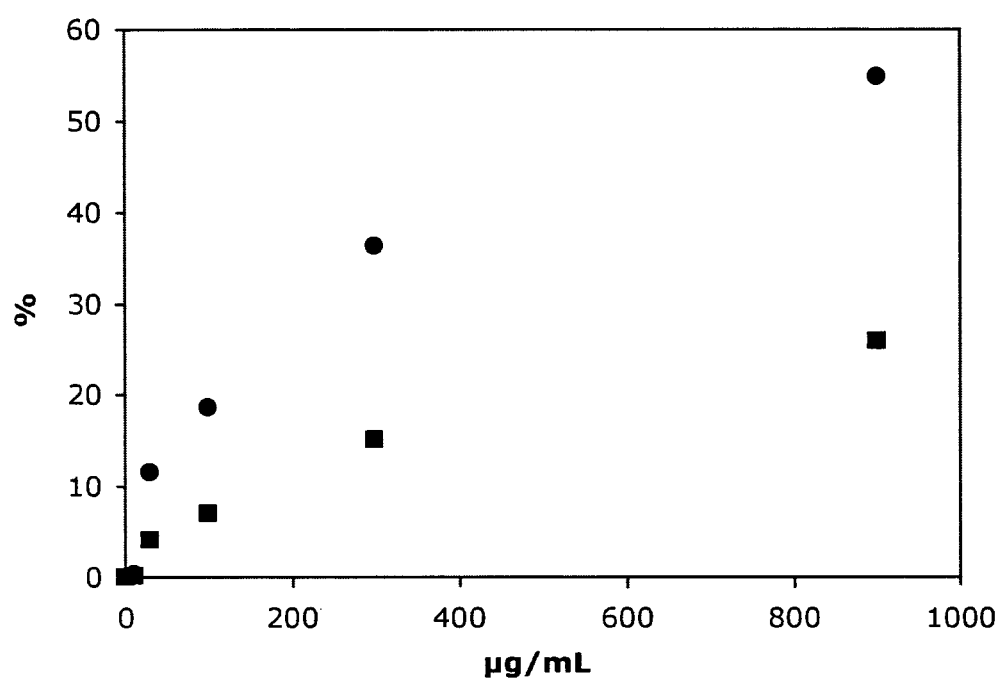
FIG. 7 illustrates a graph showing variation in the adsorption of the radiolabeled $^3$H—S-propranolol imprinting molecule on a molecularly imprinted polymer (MIP) (round symbols) or on a corresponding unprinted control polymer (square symbols), depending on the variation of the polymers' concentration, according to example 2.

The obtained results are illustrated in the graph in FIG. 7. It is clear that the MIP adsorbs more $^3$H—S-propranolol than the control polymer, therefore there is creation of recognition sites by molecular imprinting.

Example 3: Molecularly Imprinted Polymer (MIP) and Preparation Process According to the Invention from Initiator D3

Figure 8:
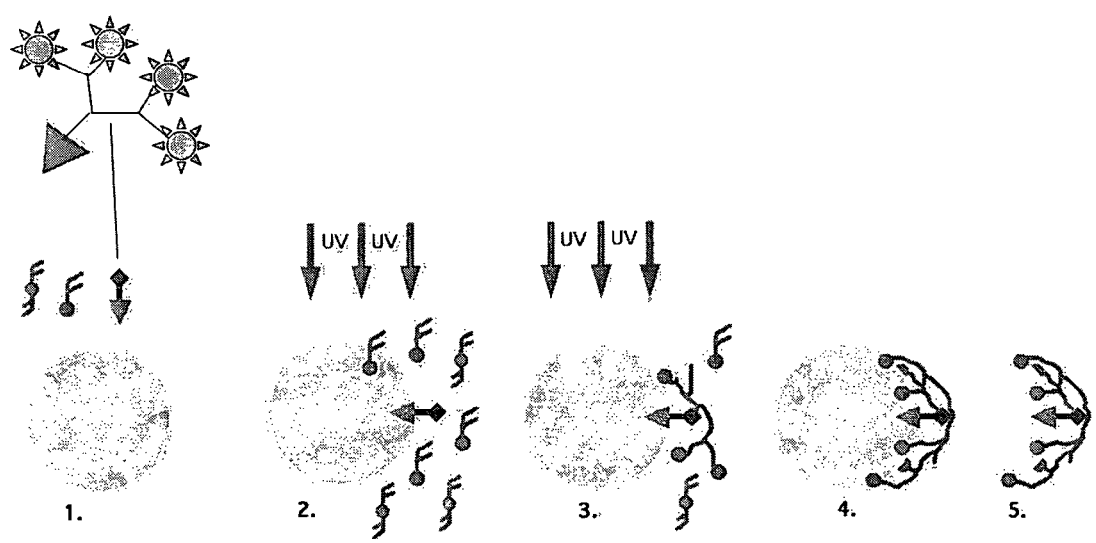
FIG. 8 illustrates a simplified diagram of an embodiment of the process aiming at manufacturing a molecularly imprinted polymer (MIP) in the form of nanoparticles the diameter of which, comprised between 20 nm and 500 nm, depends on the polymerization time for attaching the trypsin, according to example 3.

In analogy with the approach described in the example section, a MIP capable of recognizing a protein has been synthesized by the use of a dendritic initiator coupled with anchor molecules forming a stable interaction with the protein (FIG. 8).

As a non-limiting example, the trypsin protease has been chosen as an imprinting molecule, and one of its known inhibitors, benzamidine, as an anchorage molecule. Benzamidine has been coupled to the COOH grouping of the dendritic initiator D2 producing thus the molecule D3.

MIP Synthesis:

TABLE 2

Synthesis and Formulation

| Functionalities | Products | Used quantities |
|---|---|---|
| Imprinting molecule | trypsine | 17.2 mg |
| Attaching monomer | Hydroxy ethyl methacrylate (HEMA) | 54 mg |
| Cross-linked monomer | Ethylene bisacrylamide (EBA) | 128.7 mg |
| Initiator | D3 | 2.7 mg |
| Solvent | Phosphate buffer 20 mM pH 7.0 | 3.5 ml |

A solution A is prepared by weighing 17.2 mg of trypsin in 500 µl of phosphate buffer 20 mM pH 7.0 then a HEMA and EBA solution is added in 3 ml of phosphate buffer 20 mM pH 7.0. The whole is agitated gently until complete dissolution.

In the dark, a solution B is similarly prepared by weighing 2.7 mg of D3 in DMSO (100 µl). Again, the whole is agitated until complete dissolution.

In the dark, the solution A is mixed with the solution B in a glass test tube of 15 ml and is then closed with a septum cap, then gently agitated for 10 min at 4° C. The tube is placed on ice for 10 min then argon is introduced to the solution through the septum for 3 min.

The tube is irradiated with a UV lamp of 350 nm for a given period of time, at 4° C. for polymerization. The obtained suspended polymer beads are incubated at 25° C. in an urea solution 2 M (4 times for 1 h) to release the imprints from the imprinting molecules.

The evolution of MIP particles size is proportional to the photopolymerization time. The diameter is easily adaptable between 10 nm and 3 µm by adjusting the exposure time.

In order to assess the MIP and to confirm the printing effect, the particles are incubated in a tris(hydroxymethyl) aminomethan buffer 5 Mm of Ph 8.0 with a trypsin solution at 0.6 µM in a tris(hydroxymethyl)aminomethan buffer 5 mM at pH 8.0 for 2 h at 4° C. under agitation. After centrifugation to cause the particles to settle, the trypsin concentration in the supernatant is determined by measuring its catalytic activity by means of UV-visible double-beam spectrophotometer or fluorescence spectrophotometer using respectively a chromogenic substrate (chloride of $N_\alpha$-Benzoyl-L-arginine 4-nitroanilide) or a fluorogenic substrate (chloride of Boc-Gln-Ala-Arg-7-amido-4-methylcoumarin).

It is observed that the MIP adsorbs more trypsin than the control polymer, therefore there is creation of recognition sites by molecular printing.

Example 4: Molecularly Imprinted Polymer (MIP) Associated to a Solid Surface and Preparation Process According to the Invention from Initiator D2

Figure 11:
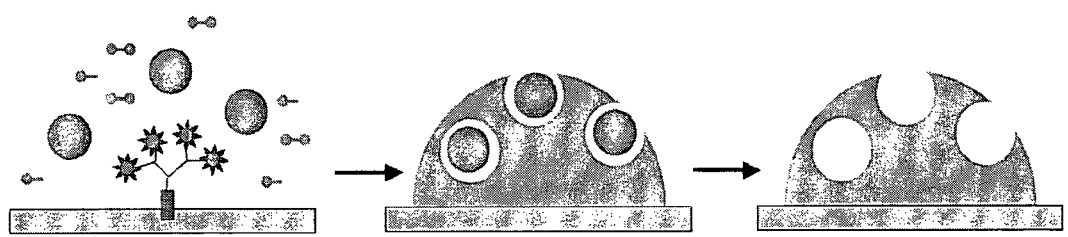
FIG. 11 illustrates a simplified diagram of the process embodiment used in FIG. 3, wherein the initiator is immobilized on a surface (example 4).

In analogy with the approach described in example 2, an MIP directly associated to a solid substrate surface has been synthesized. The example describes the synthesis on a glass surface of a selective MIP for the S-propranolol beta-blocking. The formulation used in this example is similar to the one used in example 2, except that the initiator molecule D2 is chemically immobilized at a solid substrate surface before polymerization (FIG. 11).

On a glass substrate, are successively placed a first layer 2 nm thick of chromium as a initiator layer useful for assisting the deposition of a second layer 47 nm gold-thick. The two layers can be deposed by any technique usually known by the person skilled in the art, preferably by evaporation. The surface is then incubated in a solution of 5 mM of cysteamine in ethanol for 8 h at 20° C., after which time it is rinsed with ethanol and dried under nitrogen flow. After the first incubation, the surface is again incubated into a solution containing the initiator D2 (0.1 mmol), of hydroxybenzothiazole (0.1 mmol) and N,N-diisopropylcarbodiimide (0.1 mmol) in 3 ml DMF anhydrous, under agitation for 12 h at 20° C. The surface is then rinsed with DMF then methanol, and dried under nitrogen flow.

MIP Synthesis

TABLE 3

Formulations and reagents

| Functionalities | Products | Used quantities |
|---|---|---|
| Imprinting molecule | S-propranolol | 10 mg |
| Attaching monomer | methacrylic acid | 17.0 µl |
| Cross-linked monomer | Ethylene glycol dimethacrylate | 145.0 µl |
| Initiator | — | — |
| Solvent | acetonitrile | 1.0 ml |

A solution is prepared by weighing 10 mg of S-propranolol which is then dissolved in 1 ml of acetonitrile, then 17 µl of methacrylic acid and the 145 µl of ethylene glycol dimethacrylate are added. The whole is placed in an ultrasound bath until complete dissolution. Argon is then introduced into the mixture for polymerization. Then, the mixture is placed on the substrate coated with gold then covered by a glass slide. The polymerization is initiated by irradiating the reaction mixture by means of UV lamp of 350 nm. After an appropriate time duration for polymerization (between a few seconds and a few minutes depending on the desired thickness), a thin MIP film is obtained on the golden surface.

Variant 1:

A glass or silicon substrate is used instead of the substrate covered by chromium and golden layer, and which is beforehand functionalized with aminopropyl trimethoxysilane in order to introduce amino groups for the coupling of initiator D2. The glass surface is rinsed with ethanol then with milli-Q water. Then it is placed in an ammonia bath (4.6% grade) and brought at 80° C. It is placed afterwards in peroxide hydrogen bath (5% grade) for 5 minutes at 80° C. Then, it is placed in a solution containing peroxide hydrogen (4.3% grade) and hydrochloric acid (5.3% grade) at 80° C. for 5. The glass surface is then rinsed twice with milli-Q water, twice with acetone and twice with toluene. It is afterwards placed in a solution containing 50 ml of toluene and 1 ml of aminopropyl trimethoxysilane for 12 h at 20° C. in a closed container. Then, the surface is rinsed three times with acetone and later dried under nitrogen flow. The coupling of initiator D2 is then made by incubating the surface into a solution containing D2 (0.1 mmol), hydroxybenzothiazole (0.1 mmol) and diisopropylcarbodiimide (0.1 mmol) in 3 ml anhydrous DMF, under agitation for 12 h at 20° C. The surface is rinsed afterwards with DMF then with methanol, and dried under nitrogen flow.

Variant 2:

At the moment of coupling by diisopropylcarbodiimide, an excess of acetic acid (compared with the number of D2 moles) is added to the mixture, resulting in the spacing of initiator molecules grafted on the substrate surface. For example, 0.099 mmol of acetic acid and 0.001 mmol of d2 are used. This results in obtaining nano-islands sheet rather than a continuous film on the surface.

Example 5: Molecularly Imprinted Polymer (MIP) and Preparation Process According to the Invention from Initiator D5

This example describes the synthesis of a molecularly imprinted polymer (MIP) for the S-propranolol target molecule by using initiator D5. In this example, the monomers' concentrations are selected so as to obtain molecularly imprinted polymer nanometric-sized beams.

MIP Synthesis

TABLE 2

Formulations and reagents

| Functionalities | Products | Used quantities |
| --- | --- | --- |
| Imprinting molecule | S-propranolol | 12.0 mg |
| Attaching monomer | Methacrylic acid | 31.2 µl |
| Cross-linked monomer | Ethylene glycol dimethacrylate | 348.0 µl |
| Initiator | D5 | 0.67 mg |
| Solvent | acetonitrile | 2000 µl |

A solution A is prepared by weighing 12.0 mg of S-propranolol which is then dissolved in 1 ml of acetonitrile, 31.2 µM of methacrylic acid and 348 µl of ethylene glycol dimethacrylate are added afterwards. The whole is placed in an ultrasound bath until complete dissolution.

A solution B is similarly prepared by weighing 0.204 µmol of D5 which is then dissolved in 1 ml of acetonitrile.

The whole is placed again in an ultrasound bath until complete dissolution.

In the dark, the solution A is mixed with the solution B in a glass test tube of 4 ml, then the tube is closed with a septum cap. The glass tube is placed on ice for 10 min then argon is introduced in the solution through the septum for 2 min.

The tube is placed at 10° C. and is irradiated with a UV lamp of 365 nm for 15 min for polymerization. The suspended polymer nano-beams obtained are incubated at 25° C. into the methanol/acetic acid mixtures 4:1 (3 times for 1 h) and into methanol (3 times for 1 h). This treatment allows the releasing of the imprints of the obtained molecularly imprinted polymer.

MIP Characteristics and Properties

Figure 12:
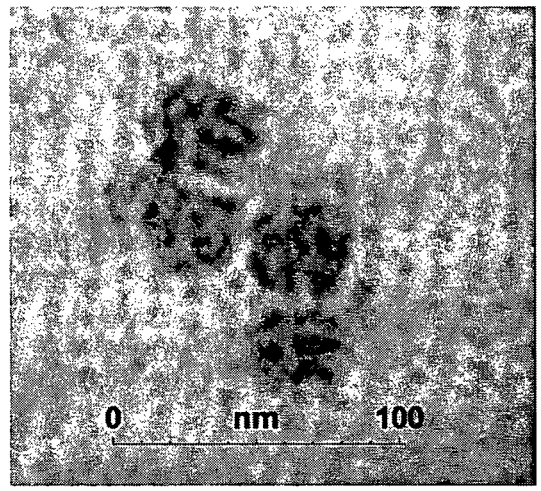
FIG. 12 illustrates an image taken, using transmission electron microscopy imagery, of MIP particles obtained by the process according to the present invention and according to example 5 (at the top); the middle graph shows the result of a particles' analysis by dynamic light scattering: the variation of the percentage of intensity with regard to the particle's size; the bottom graph shows the variation of the adsorption of the radiolabeled $^3$H—S-propranolol imprinting molecule on a molecularly imprinted polymer (MIP) specific for the S-propranolol (filled round symbols) or on a corresponding unprinted control polymer (empty round symbols), depending on the variation of the polymers' concentration, according to example 5.
Figure 12:
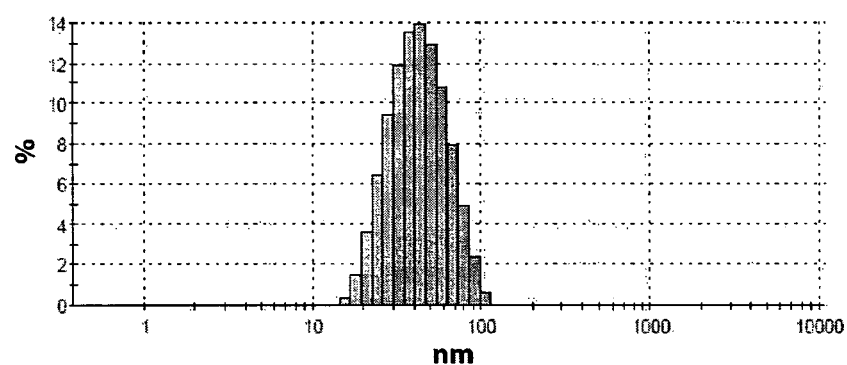
Figure 12:
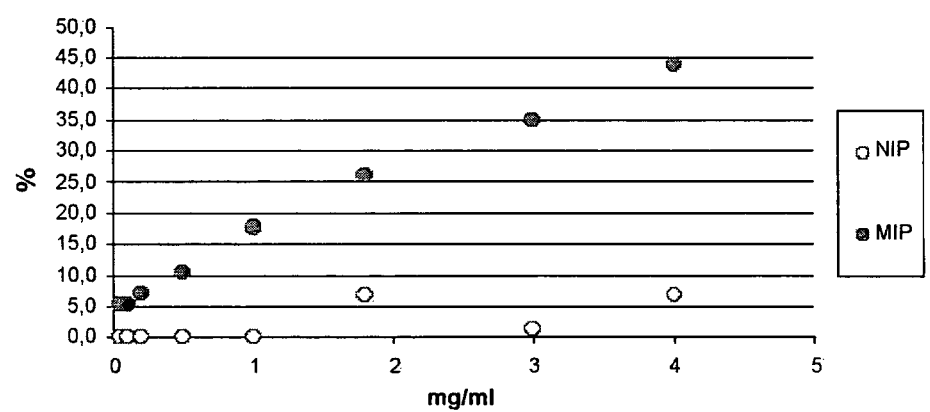

FIG. 12 illustrates an image of MIP spherical particles obtained according to the invention, by means of transmitting electron microscopy. It is noted that the diameter of the formed particles is about 50 nm. In FIG. 12, the center graph illustrates the analysis of the MIP particles by dynamic light diffusion. An average size of 45 nm and a low polydispersity are noted. If the same synthesis is made by an identical method but by implementing a multifunctional initiator, benzyl-N,N-dimethyldithiocarbamate, the total number of dithiocarbamate functionalities being the same in both cases, no MIP particles are obtained after synthesis. It is clearly observed that the use of initiator D5 allows to obtain MIP nano-particles unlike the mono-functional initiator, benzyl-N,N-dimethyl dithiocarbamate.

To assess the molecularly printing effect, the MIP and a control polymer chemically identical but synthesized in the absence of S-propranolol are incubated with propranolol tritium labeled ($^3$H—S-propranolol). To this end, in two series of test tubes of 1.5 ml, increasing quantities (from 100 to 4000 µg) of MIP and control polymer, are introduced, respectively, suspended into the acetonitrile. To this suspension is added 1 pmol of $^3$H—S-proranolol, then the tubes are incubated under agitation for 2 h at 25° C. After centrifugation, the radioactivity in the supernatant is determined by scintillation counting in liquid phase. The obtained value corresponds to $^3$H—S-propranolol, not linked to the polymer, and the linked fraction is calculable by the difference between the quantity of $^3$H—S-propranolol found in the supernatant and the quantity of total $^3$H—S-propranolol added to each test tube.

The obtained results are illustrated in the bottom graph of FIG. 12. It is clear that the MIP adsorbs more $^3$H—S-propranolol than the synthesized control polymer without the imprinting molecule $^3$H—S-propranolol, so there is creation of recognition sites by molecular imprint.

Example 6: Molecularly Imprinted Polymer (MIP) and Preparation Process According to the Invention from Initiator D5

This example describes the synthesis of the molecularly imprinted polymer (MIP) for the target S-propranolol molecule by the use of initiator D5. In this example, the monomers' concentrations are selected so as to obtain nanometric sized beams of molecularly imprinted molecules.

MIP Synthesis

TABLE 2

Formulations and reagents

| Functionalities | Products | Used quantities |
| --- | --- | --- |
| Imprinting molecule | S-propranolol | 12.0 mg |
| Attaching monomer | Methacrylic acid | 31.2 µl |
| Cross-linked monomer | Ethylene glycol dimethacrylate | 348.0 µl |
| Initiator | D5 | 6.7 mg |
| Solvent | acetonitrile | 10.5 ml |

A solution A is prepared by weighing 12.0 mg of S-propranolol which is then dissolved in 5 ml of acetonitrile, 31.2 µM of methacrylic acid and 348 µl of ethylene glycol dimethacrylate are added afterwards. The whole is placed in ultrasound bath until complete dissolution.

A solution B is prepared, similarly, by weighing 2.04 µmol of D5 which is then dissolved in 5.5 ml of acetonitrile.

The whole is placed again in ultrasound bath until complete dissolution.

In the dark, solution A is mixed with solution B in a glass test tube of 15 ml and then the tube is closed by a septum cap. The tube is placed afterwards in ice for 10 min then argon is introduced in the solution through the septum for 2 min.

The tube is placed at 30° C. and is irradiated with a UV lamp of 365 nm for 16 h for polymerization.

A polymerization yield is obtained, here expressed in terms of % monomers conversion, of 21%. If the same synthesis is made by an identical method but by implementing a mono-functional initiator, benzyl-N,N-dimethyldithiocarbamate, the total number of dithiocarbamate functionalities is only 5%. It is clear that the use of initiator D5 allows to obtain MIP nanoparticles with a higher yield compared to the mono-functional initiator, benzyl-N,N-dimethyldithiocarbamate.

LIST OF REFERENCES

[1] K. Mosbach, O. Ramström, Bio/Technology 1996, 14, 163-170.
[2] B. Rückert, A. Hall, B. Sellergren, J. Mater. Chem. 2002, 12, 2275-2280.
[3] A. Biffis, N. B. Graham, G. Siedlaczek, S. Stalberg, G. Wulff, Macromol. Chem. Phys. 2001, 202, 163-171.
[4] M. Antonietti, C. Rosenauer, Macromolecules 1991, 24, 3434-3442.
[5] G. Wulff, B.-O. Chong, U. Kolb, Angew. Chem. Int. Ed. 2006, 45, 2955-2958.
[6] T. Otsu, J. Polym. ScL: Part A: Polym. Chem. 2000, 38, 2121-2136.
[7] R. C. Mehrotra, "Présent status and future potential of the Sol-Gel process", dans Chemistry, Spectroscopy and Applications of Sol-Gel Glasses, Vol. 77 de la série Structure and Bonding, Springer, Berlin/Heidelberg, 1992.
[8] R. H. Schmidt, K. Haupt (2005), Chem. Mater. 17, 1007-1016.
[9] Y. Ju, D. Kumar, R. S. Varma, J. Org. Chem., 2006, 71, 6697-6700.
[10] G. R. Gale G R, L. M. Atkins, E. M. Walker Jr, A. B. Smith, M. M. Jones, Ann. Clin. Lab. Sci. 1983, 13, 474-481.
[11] H. C. Kolb, K. B. Sharpless, Drug Discov. Today, 2003, 8, 1128-1137.
[12] H. C. Kolb, M. G. Finn, K. B. Sharpless, K. B. Angew. Chem. In Ed., 2001, 40, 2004-2021.

The invention claimed is:

1. A method for preparing a molecularly imprinted polymer by radical polymerization, the method comprising:
contacting at least one imprinting molecule or entity, one or more identical or different monomers capable of forming the molecularly imprinted polymer, and at least one molecular initiator having more than four chemical functionalities, each of the more than four chemical functionalities on the at least one molecular initiator capable of forming one or more radicals for initiating a polymerization of the one or more monomers over or around the at least one imprinting molecule or entity, wherein the at least one molecular initiator having more than four chemical functionalities is selected from the group consisting of Formula D1, D2, D3, D4, D5, and D6:

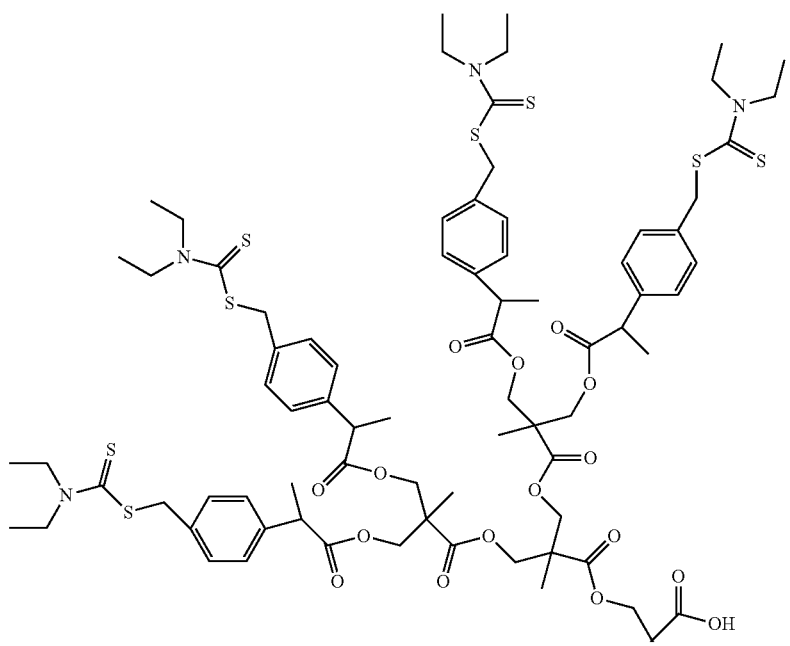

D1

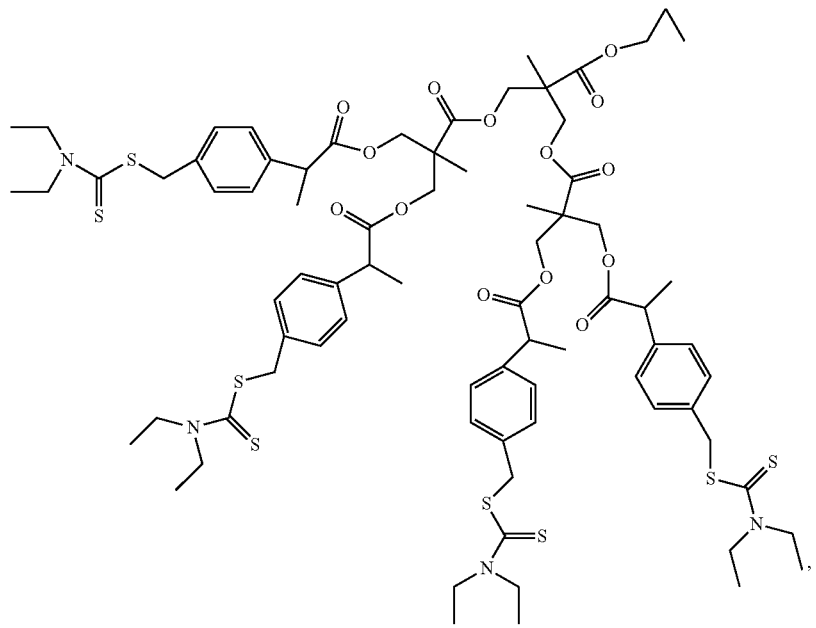
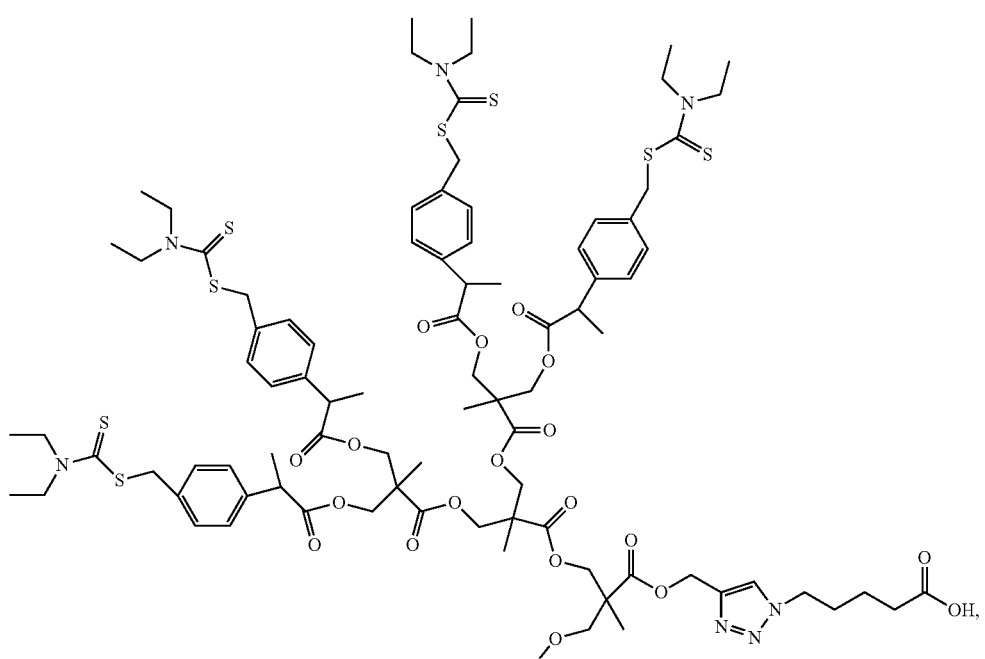
D2

-continued
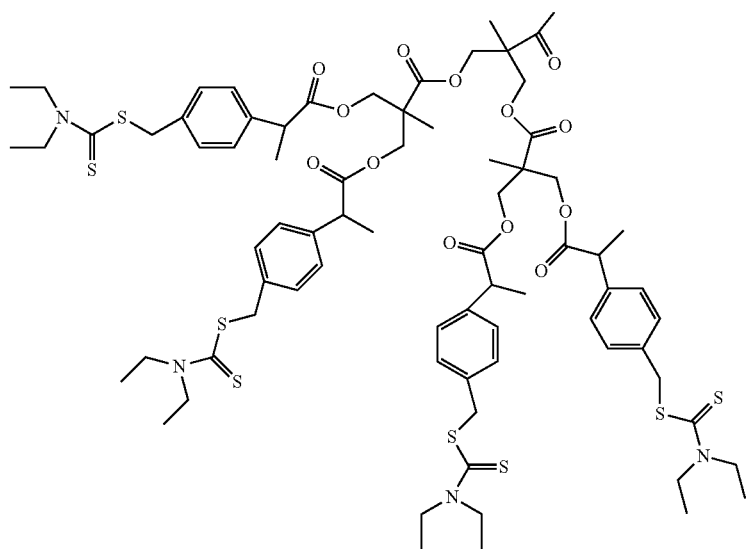
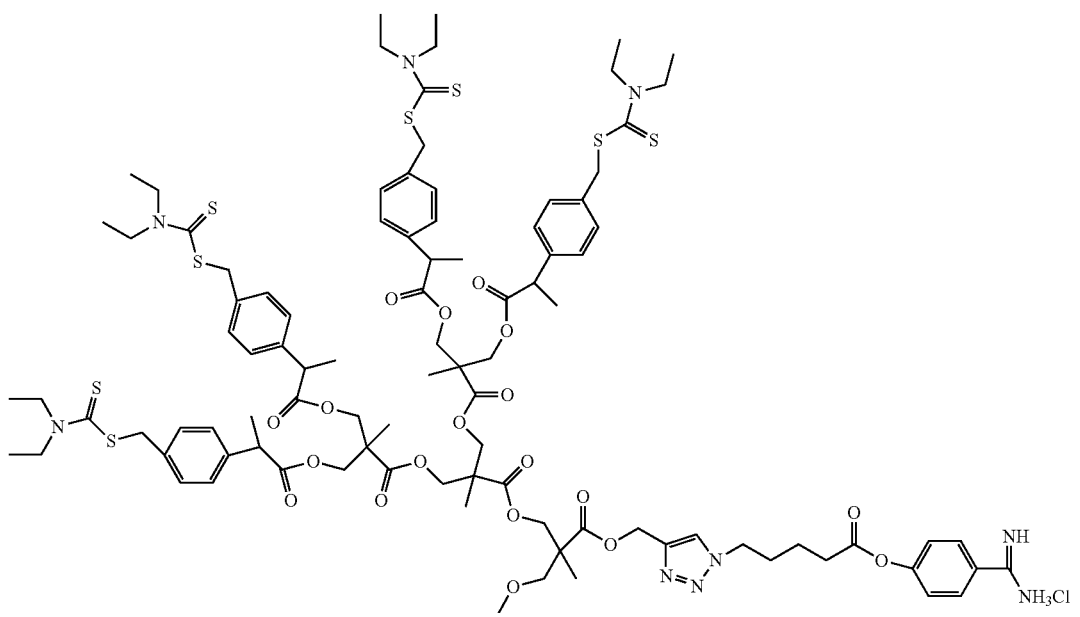
D3

-continued
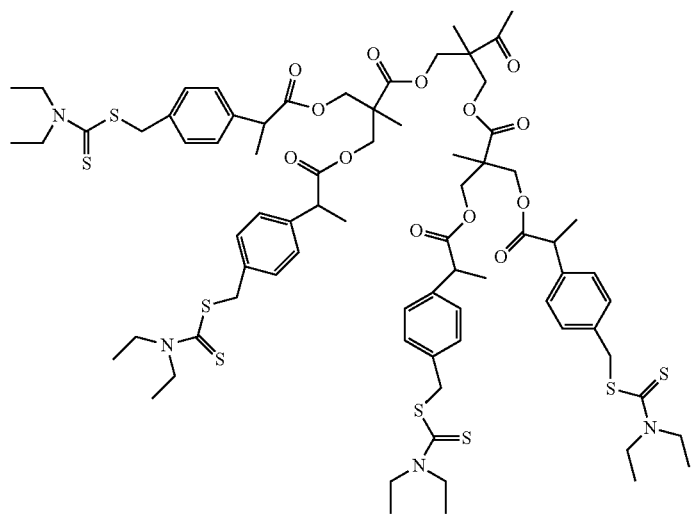
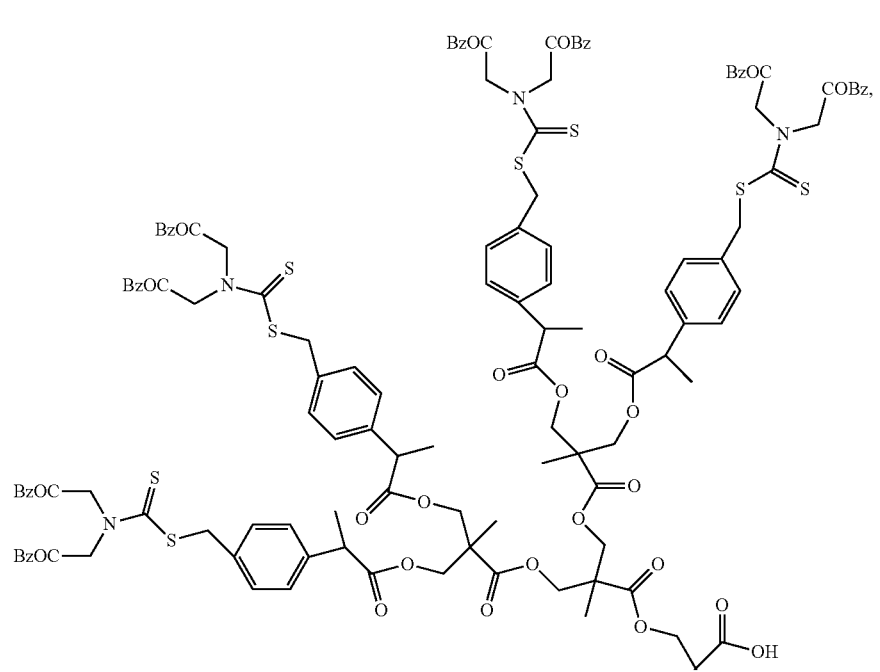
D4

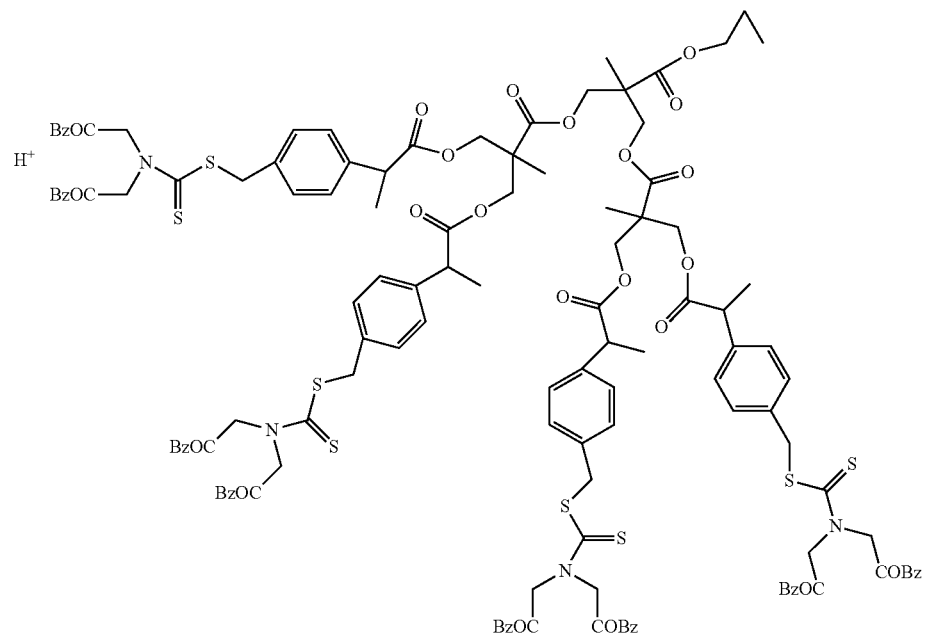
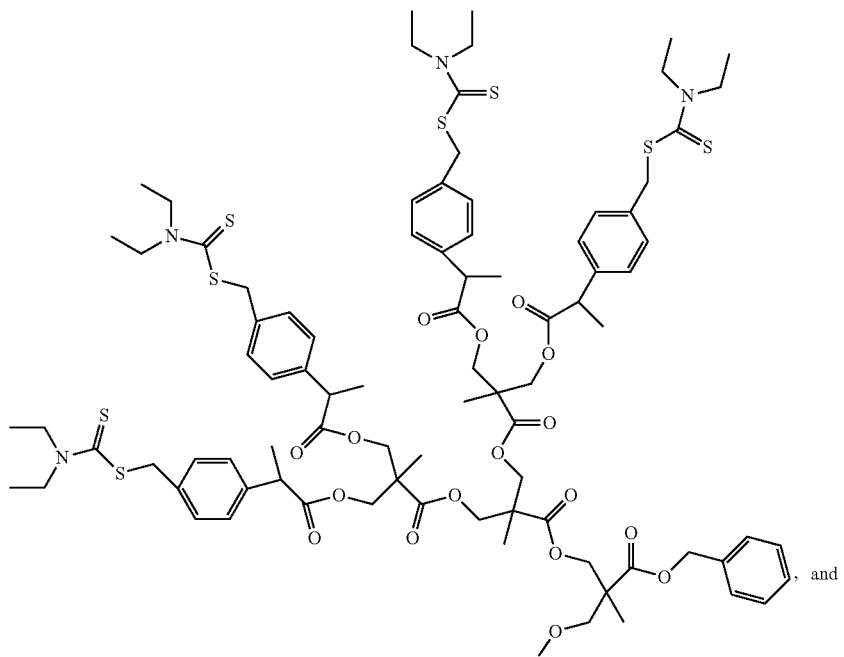
D5

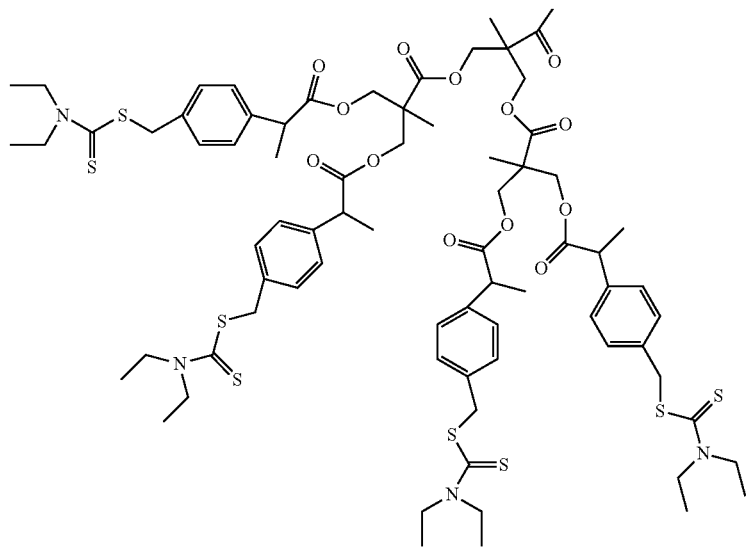
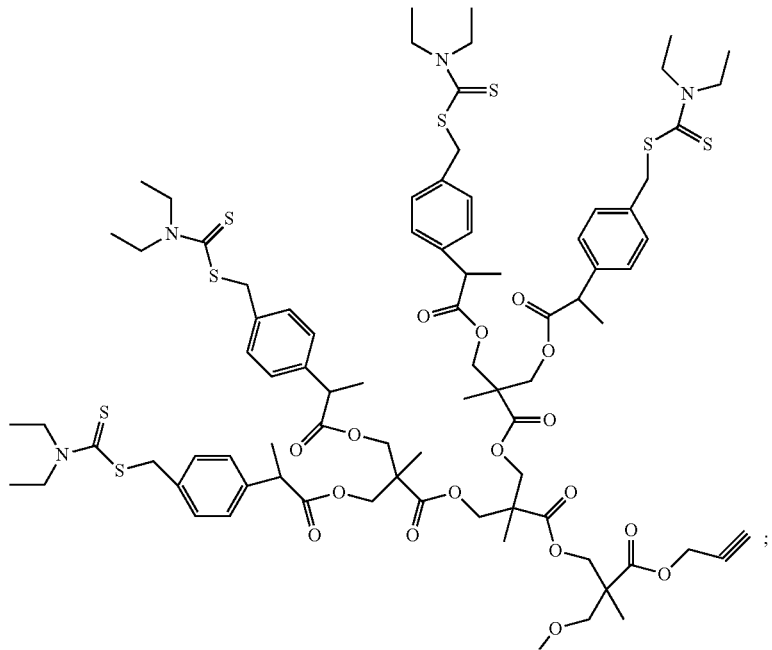
D6

-continued

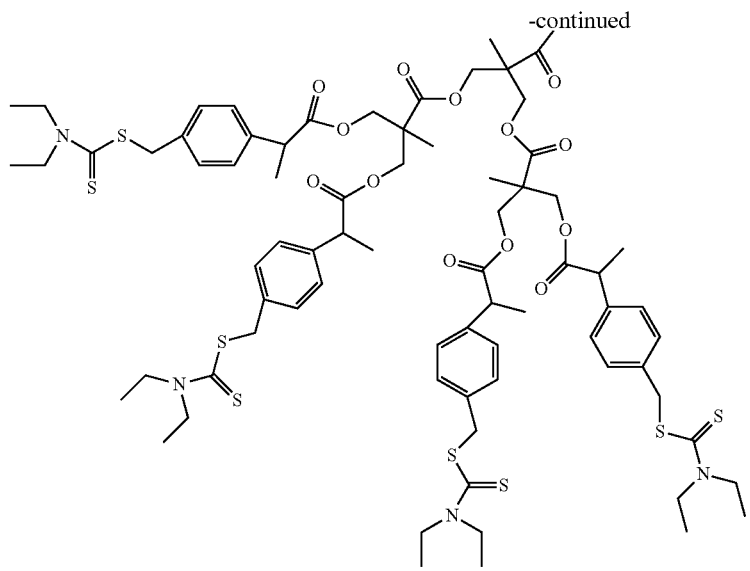

performing radical polymerization of one or more identical or different monomers over or around the at least one imprinting molecule or entity under exposure of a light irradiation of wavelength ranging between 100 nm and 1200 nm or a supply of thermal energy to form the molecularly imprinted polymer over or around the at least one imprinting molecule or entity; and removing from the molecularly imprinted polymer formed during the radical polymerization with at least one solvent the monomers that are not polymerized, all of the imprinting molecule or entity, a portion of the imprinting molecule or entity, the monomers that are not polymerized and all of the imprinting molecule or entity, or the monomers that are not polymerized and a portion of the imprinting molecule or entity;

wherein the at least one molecular initiator is not immobilized at a solid substrate surface before the radical polymerization.

2. The method according to claim 1, wherein the at least one imprinting molecule or entity is selected from the group consisting of amino acids, monosaccharide, lipids, nucleosides, nucleotides, oligomers and polymers obtained from entities or molecules, peptides, proteins, nucleic acids, oligosaccharides, polysaccharides, biologically active entities or molecules, drugs, antibiotics, steroids, vitamins, toxins, enzymes, doping agents, pesticides, insecticides, fungicides, herbicides, explosive substances, toxic substances, endocrine disruptors, bacterial mycotoxins, nanoparticles, prokaryotic bacteria cells, eukaryotic bacteria cells, animal cells, yeast cells, fungus cells, human cells, animal cells, plant cells, viruses, and cellular tissues.

3. The method according to claim 1, wherein the at least one imprinting molecule or entity is selected from the group consisting of trypsin, kallikrein, S-propranolol, theophyllin, 2,4-dichlorophenoxyacetic acid, beta-estradiol, testosterone, atrazine, morphine, cocaine, and tetrahydrocannabinol.

4. The method according to claim 1, the method further comprising adding a substrate prior to performing the radical polymerization.

5. The method according to claim 4, wherein the substrate is selected from the group consisting of glass, quartz, mica, silicon, germanium, silicon carbide, tin-indium oxide, titanium dioxide, aluminum oxide, a cross-linked organic polymer, polystyrene, poly(styrene-co-methacrylate), poly(methyl methacrylate), poly(acrylonitrile), polyamide, polyester, polyurethane, poly(dimethyl siloxane), polybutadiene, a metal, gold, silver, platinum, and a composite of two or more thereof.

6. The method according to claim 1, wherein the one or more identical or different monomers comprises one or more binding monomers and one or more cross-linking monomers, and wherein the one or more binding monomers are capable of bonding with at least one of the one or more cross-linking monomers when the one or more binding monomers are mixed with the one or more cross-linking monomers.

7. The method according to claim 6, wherein the one or more identical or different monomers include at least a vinyl functionality selected from the group consisting of methacrylic acid, trifluoromethylacrylic acid, acrylic acid, itaconic acid, styrenesulfonic acid, acrylamidopropanesulfonic acid, 4-vinylphenolyl boronic acid, 4-vinylbenzoic acid, carboxyethylacrylate, hydroxyethyl methacrylate phosphate, 2-vinylpyridine, 4-vinylpyridine, 1-vinylimidazole, 4(5)-vinylimidazole, 2-aminoethyl methacrylate, 2-(dimethylamino)ethyl methacrylate, aminoethyl acrylate, 4-vinylbenzyl trimethylammonium chloride, hydroxyethyl methacrylate, glycidyl methacrylate, acrylamide, methacrylamide, isopropylacrylamide, 4-vinylbenzamidine, 4-methacrylamidobenzamidine, styrene, phenyl methacrylate, cyclohexyl methacrylate, methyl methacrylate, butyl methacrylate, hexyl methacrylate, octyl methacrylate, ethylene glycol dimethacrylate, hexanediol dimethacrylate, trismethylolpropane trimethacrylate, polyethylene glycol dimethacrylate, triethylene glycol dimethacrylate, pentaerythritol triacrylate, divinylbenzene, ethylene bisacrylamide, methylene bisacrylamide, bisacryloyl piperazine, N,N-bisacryloylcystamine, N,N-1,2-dihydroxyethylene bisacrylamide, N,O-bismethacryloyl ethanolamine, and mixtures thereof.

8. The method according to claim 1, further comprising synthesizing the at least one molecular initiator prior to the contacting step.

9. The method according to claim 8, the method further comprising mixing the at least one molecular initiator with a sensitizer selected from the group consisting of acridines, Acriflavine, Acridine Orange, phenazines, Safranine O, oxazines, thiazines, methylene blue, thionine, xanthenes, Eosine Y, Rose Bengal, Erythrosyne, rhodamines, thioxanthenes, polymethines, isopropylthioxanthone, chlorothioxanthone, couramines, and keto-coumarines.

10. The method according to claim 1, wherein the contacting step is conducted in the presence of at least one porogenic solvent selected from the group consisting of benzene, toluene, xylene, chlorinated solvents, chloroform, dichloromethane, dichloroethane, 1,1,2,2-tetrachloro ethane, perfluorated solvents, hexafluorocyclohexane, ethers, tetrahydrofuran, diethylene glycol dimethyl ether, triethylene glycol dimethyl ether, amides, dimethylformamide, formamide, nitriles, acetonitrile, caprylonitrile, ketones, acetone, esters, ethyl acetate, alkanes, hexane, heptanes, alcohols, methanol, ethanol, isopropanol, butanol, decanol, water, and mixtures thereof.

11. The method according to claim 1, wherein performing the radical polymerization is performed under exposure to light irradiation of visible wavelength or UV wavelength ranging between 150 nm and 750 nm.

12. The method according to claim 1, wherein performing the radical polymerization is performed with the supply of thermal energy at a temperature between 0° C. and 200° C.

13. The method according to claim 1, wherein the at least one solvent is selected from the group consisting of water, methanol, ethanol, isopropanol, acetonitrile, chloroform, heptanes, toluene, acetic acid, mixtures thereof, and supercritical $CO_2$.

14. The method according to claim 1, wherein the at least one solvent to remove the imprinting molecule or entity from the molecularly imprinted polymer formed during the radical polymerization contains an agent selected from the group consisting of a detergent, sodium dodecylsulfate, cetyltrimethylammonium bromide, urea, trifluoroacetic acid, triethylamine, a hydrolytic enzyme comprising a peptidase or a protease, trypsin, proteinase K, a nuclease, *Staphylococcus aureus* nuclease, ribonuclease A, a lipase, porcine pancreatic lipase, *Pseudomonas* sp. Lipase XIII, a glycosidase, beta-glucosidase, alpha-glucosidase, beta-galactosidase, a salt, and sodium thiosulfate.

15. The method according to claim 1, further comprising applying an electrical field to remove the at least one imprinting molecule or entity from the molecularly imprinted polymer formed during the radical polymerization.

* * * * *